United States Patent
Soreq et al.

(10) Patent No.: US 7,494,783 B2
(45) Date of Patent: Feb. 24, 2009

(54) METHOD FOR ASSESSING TRAIT ANXIETY BY DETERMINING CHOLINERGIC STATUS

(75) Inventors: Hermona Soreq, Jerusalem (IL); Ella Sklan, Rechovot (IL); Raz Yirmiya, Jerusalem (IL); Keren Ailon, Givat-YeArim (IL); Irit Shapira-Lichter, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 177 days.

(21) Appl. No.: 11/400,224

(22) Filed: Apr. 10, 2006

(65) Prior Publication Data
US 2007/0037241 A1 Feb. 15, 2007

Related U.S. Application Data

(63) Continuation-in-part of application No. PCT/IL2004/000933, filed on Oct. 10, 2004.

(60) Provisional application No. 60/510,560, filed on Oct. 10, 2003.

(51) Int. Cl.
*C12Q 1/46* (2006.01)
(52) U.S. Cl. ..................................................... 435/20
(58) Field of Classification Search ................... 435/20
See application file for complete search history.

(56) References Cited

U.S. PATENT DOCUMENTS

| | | | |
|---|---|---|---|
| 4,683,202 A | 7/1987 | Mullis | |
| 6,300,063 B1 | 10/2001 | Lipshutz et al. | |
| 6,746,850 B2 * | 6/2004 | Feaster et al. | 435/20 |
| 2002/0009730 A1 | 1/2002 | Chenchick et al. | |
| 2003/0036632 A1 | 2/2003 | Soreq et al. | |
| 2003/0082548 A1 | 5/2003 | Shu et al. | |
| 2003/0162207 A1 | 8/2003 | Comings et al. | |
| 2003/0175210 A1 * | 9/2003 | Leyland-Jones | 424/9.2 |

FOREIGN PATENT DOCUMENTS

| | | |
|---|---|---|
| EP | 0717113 | 6/1996 |
| EP | 0730663 | 9/1996 |
| WO | WO 92/15712 | 9/1992 |
| WO | WO 97/02102 | 1/1997 |
| WO | WO 97/04127 | 2/1997 |
| WO | WO 97/29212 | 8/1997 |
| WO | WO 2004/029290 | 4/2004 |
| WO | WO 2004/029290 A2 * | 4/2004 |

OTHER PUBLICATIONS

Sklan E. et al. Acetylcholinesterase/Paraoxonase Genotype and Expression Predict Anxiety Scores . . . PNAS 101(15)5512-17, Apr. 13, 2004.*
Mathew R. et al. True and Pseudo Cholinesterases in Depression. American J Psychiatry 139(1)125-127, 1982.*
Modai I. et al. Serum Pseudocholinesterase in State Anxiety. J Clinical Psychiatry 48(5)204-6, May 1987.*
Abrams et al. "Comprehensive Detection of Single Base Changes in Human Genomic DNA Using Denaturing Gradient Gel Electrophoresis and A GC Clamp", Genomics, 7: 463-475, 1990.
Abravaya et al. "Detection of Point Mutations With A Modified Ligase Chain Reaction (Gap-LCR)", Nucleic Acids Research, 23(4); 675-682, 1995.
Abravaya et al. "Molecular Beacons as Diagnostic Tools: Technology and Applications", Clinical and Chemical Laboratory Medicine, 41(4): 468-474, 2003.
Akhmedova et al. "Paraoxonase 1 Met-Leu 54 Polymorphism Is Associated With Parkinson's Disease", Journal of Neurological Sciences, 184(2); 179-182, 2001. p. 180, col. 1-2, § 2, p. 181, col. 1-2, § 3, Abstract.
Akula et al. "Utility and Accuracy of Template-Directed Dye-Terminator Incorporation With Fluorescence-Polarization Detection for Genotyping Single Nucleotide Polymorphisms", BioTechniques, 32(5): 1072-1078, 2002.
Anisman et al. "Cytokines, Stress and Depressive Illness: Brain-Immune Interactions", Annal of Medicine, 35: 2-11, 2003.
Aviram et al. "Paraoxonase Inhibits High-Density Lipoprotein Oxidation and Preserves Its Functions", Journal of Clinical Investigation, 101(8): 1581-1590, 1998.
Balciuniene et al. "Investigation of the Functional Effect of Monoamine Oxidase Polymorphisms in Human Brain", Human Genetics, 110: 1-7, 2002.
Barany "Genetic Disease Detection and DNA Amplification Using Cloned Thermostable Ligase", Proc. Natl. Acad. Sci. USA, 88: 189-193, 1991.
Bartels et al. "Mutation at Codon 322 in the Human Acetylcholinesterase (ACHE) Gene Accounts for YT Blood Group Polymorphism", American Journal of Human Genetics, 52(5): 928-936, 1993.
Beaudet et al. "Homogeneous Assays for Single-Nucleotide Polymorphism Typing Using AlphaScreen", Genome Research, 11: 600-608, 2001.
Bell et al. "SNPStream® UHT: Ultra-High Throughput SNP Genotyping for Pharmacogenomics and Drug Discovery", BioTechniques Supplements, 32: S70-S77, 2002.
Bernik et al. "Pharmacological Stimulation of the Cholinergic Antiinflammatory Pathway", Journal of Experimental Medicine, 195(6): 781-788, 2002.
Birikh et al. "Interaction of 'Readthrough' Acetylcholinesterase With RACK1 and PKCβII Correlates With Intensified Fear-Induced Conflict Behavior", Proc. Natl. Acad. Sci. USA, 100(1): 283-288, 2003.
Blatter Garin et al. "Paraoxonase Polymorphism Met-Leu54 Is Associated With Modified Serum Concentrations of the Enzyme", Journal of clinical Investigation, 99(1): 62-66, 1997.

(Continued)

*Primary Examiner*—Ralph Gitomer

(57) ABSTRACT

The invention provides methods/kits for assessing levels of trait or state anxiety in a subject by comparing genotypes and/or expression patterns at the ACHE, PON1 and/or BChE genes to the genotype and/or expression pattern of the genes in a reference population whose genotype and/or expression pattern of the genes is known or by correlating AChE levels activity to those of PON.

16 Claims, 13 Drawing Sheets
(5 of 13 Drawing Sheet(s) Filed in Color)

OTHER PUBLICATIONS

Blatter Garin et al. "Paraoxonase Polymorphism Met-Leu54 Is Associated With Modified Serum Concentrations of the Enzyme", Journal of Clinical Investigations, 99(1): 62-66, 1997. p. 63, col. 1, Lines 10-65, Abstract.

Blumenthal et al. "Contribution of Job Strain, Job Status and Marital Status to Laboratory and Ambulatory Blood Pressure in Patients With Mild Hypertension", Journal of Psychosomatic Research, 39(2): 133-144, 1995.

Børresen et al. "Constant Denaturant Gel Electrophoresis as A Rapid Screening Technique for P53 Mutations", Proc. Natl. Acad. Sci. USA, 88: 8405-8409, 1991.

Bouchard et al. "Aims, Design, and Measurement Protocol", Medicine and Science in Sports and Exercise, 27: 721-729, 1995.

Brenner et al. "The role of Readthrough Acetylcholinesterase in the Pathophysiology of Myasthenia Gravis", The FASEB Journal, 17: 214-222, 2003.

Brophy et al. "Effects of 5' Regulatory-Region Polymorphisms on Paraoxonase-Gene (PON1) Expression", American Journal of Human Genetics, 68: 1428-1436, 2001.

Carmine et al. "Further Evidence for An Association of the Paraoxonase 1 (PON1) Met-54 Allele With Parkinson' Disease", Movement Disorders, 17(4): 764-766, 2002. p. 765, Table 1, col. 1, Line 34-col. 2, Line 29.

Cashman et al. "Population Distribution of Human Flavin-Containing Monooxygenase Form 3: Gene Polymorphisms", Drug Metabolism and Disposition, 29(12): 1629-1637, 2001.

Cohen et al. "Endotoxin-Induced Changes in Human Working and Declarative Memory Associate With Cleavage of Plasma "Readthrough" Acetylcholinesterase", Journal of Molecular Neuroscience, 21: 199-212, 2003.

Cohen et al. "Neuronal Overexpression of 'Readthrough' Acetylcholinesterase Is Associated With Antisense-Suppressible Behavioral Impairments", Molecular Psychiatry, 7: 874-885, 2002.

Conner et al. "Detection of Sickle Cell βS-Globin Allele by Hybridization With Synthetic Oligonucleotides", Proc. Natl. Acad. Sci. USA, 80: 278-282, 1983.

Costa et al. "Functional Genomics of the Paraoxonase (PON1) Polymorphisms: Effect on Pesticide Sensitivity, Cardiovascular Disease, and Drug Metabolism", Annual Reviews in Medicine, 54: 371-392, 2003.

Cotton et al. "Reactivity of Cytosine and Thymine in Single-Base-Pair Mismatches With Hydroxylamine and Osmium Tetroxide and Its Application to the Study of Mutations", Proc. Natl. Acad. Sci. USA, 85: 4397-4401, 1988.

Curcio et al. "Multiplex High-Throughput Solid-Phase Minisequencing by Capillary Electrophoresis and Liquid Core Waveguide Fluorescence Detection", Electrophoresis, 23: 1467-1472, 2002.

Curley et al. "Isoform—Specific Effects of Apoe on Anxiety in Probable Ad Patients and Apoe-/- Mice", 2002: P. Abstract No. 883.2, 2002. Database BIOSIS 'Online! Bioscience Information Service, Database Acc. No. PREV200300379477 & Society for Neuroscience Abstract Viewer and Itinery Planner, vol. 2002: P.Abstract No. 883.2, 32nd Annual Meeting for the Society for Neuroscience, Orlando, Fa., USA, 2002.

Dantoine et al. "Implication des Facteurs Vasculaires dans les Troubles Cognitifs du Sujet Âgé: Relation Entre le Polymorphisme 192 de la Paraoxonase 1 et la Maladie d'Alzheimer", Revue de Medicine Interne, P.606S, 2002. Abstract.

Davies et al. "The Effect of the Human Serum Paraoxonase Polymorphism Is Reversed With Diazoxon, Soman and Sarin", Nature Genetics, 14: 334-336, 1996.

Day et al. "High-Throughput Genotyping Using Horizontal Polyacrylamide Gels With Well Arranged for Microplate Array Diagonal Gel Electrophoresis (MADGE)", BioTechniques, 19(5): 830-835, 1995.

Deustch et al. "ARP—A Novel Hematopoietic Growth Factor and Stress Signal Derived From Acetylcholinesterase", Blood, 94: 46A, 1999. Abstract.

Draganov et al. "Pharmacogenetics of Paraoxonases: A Brief Review", Naunyn-Schmiedeberg's Archives of Pharmacology, 369: 78-88, 2004.

DSM "Anxiety Disorders", Diagnostic and Statistical Manual for Mental Disorders, DSM, 4th Ed., p. 393-444, 1994.

Dunner "Management of Anxiety Disorders: The Added Challenge of Comorbidity", Depression and Anxiety, 13: 57-71, 2001.

Durrington et al. "Paraoxonase and Atherosclerosis", Arteriosclerosis, Thrombosis, and Vascular Biology, 21: 473-480, 2001.

Eckert et al. "DNA Polymerase Fidelity and the Polymerase Chain Reaction", PCR Methods and Applications, 1: 17-24, 1991.

Ehrlich et al. "Population Diversity and Distinct Haplotype Frequencies Associated With ACHE and BCHE Gene of Israeli Jews From Trans-Caucasian Georgia and From Europe", Genomics, 22: 288-295, 1994.

Ellman et al. "A New and Rapid Colorimetric Determination of Acetylcholinesterase Activity", Biochemical Pharmacology, 7: 88-95, 1961.

Faham et al. "A Novel In Vivo Method to Detect DNA Sequence Variation", Genome Research, 5: 474-482, 1995.

Fan et al. "Parallel Genotyping of Human SNPs Using Generic High-Density Oligonucleotide Tag Arrays", Genome Research, 10: 853-860, 2000.

Feingold et al. "Paraoxonase Activity in the Serum and Hepatic mRNA Levels Decrease During the Acute Phase Response", Atherosclerosis, 139: 307-315, 1998.

Fisher et al. "DNA Fragments Differing by Single Base-Pair Substitutions Are Separated in Denaturing Gradient Gels: Correspondence With Melting Theory", Proc. Natl. Acad. Sci. USA, 80: 1579-1583, 1983.

Furlong et al. "Spectrophotometric Assaus for he Enzymatic Hydrolysis of the Active Metabolites of Chlorpyrifos and Parathion by Plasma Paraoxonase/Arylesterase", Analytical Biochemistry, 180: 242-247, 1989.

Furlong et al. "The PON1 Gen and Detoxication", NeuroToxicology, 21(4): 581-588, 2000.

Gasparini et al. "Analysis of 31 CFTR Mutations by Polymerase Chain Reaction/Oligonucleotide Ligation Assay in A Pilot Screening of 4476 Newborns for Cystic Fibrosis", Journal of Medical Screening, 6: 67-69, 1999.

Germer et al. "Single-Tube Genotyping Without Oligonucleotide Probes", Genome Research, 9: 72-78, 1999.

Gogos et al. "Detection of Single Base Mismatches of Thymine and Cytosine Residues by Potassium Permanganate and Hydroxylamine in the Presence of Tetralkylammonium Salts", Nucleic Acids Research, 18(23): 6807-6817, 1990.

Grant et al. "Genomic Dissection Reveals Locus Response to Stress for Mammalian Acetylcholinesterase", Cellular and Molecular Neurobiology, 21(6): 783-797, 2001.

Holland et al. "Detection of Specific Polymerase Chain Reaction Product by Utliizing the 5'-> 3' Exonuclease Activity of Thermus Aquaticus DNA Polymerase", Proc. Natl. Acad. Sci. USA, 88: 7276-7280, 1991.

Hsu et al. "Universal SNP Genotyping Assay With Fluorescence Polarization Detection", BioTechniques, 31(3): 560, 562, 564-568, 2001.

Ihaka et al. "R: A Language for Data Analysis and Graphics", Journal of Computational and Graphical Statistics, 5(3): 299-314, 1996.

Innis et al. "Contents", PCR Protocols: A Guide to Methods and Applications, Academic Press, 7 P., 1990.

Jarvik et al. "Paraoxonase Activity, But Not Haplotype Utilizing the Linkage Disequilibrium Structure, Predicts Vascular Disease", Arteriosclerosis Thrombosis and Vascular Biology, 23(8): 1465-1471, 2003. p. 1466, col. 1, § 3-p. 1467, col. 1, § 1, p. 1468, col. 2, § 2-p. 1469, col. 2, § 1, Table 3, Fig. 2, Abstract.

Kaufer et al. "Acute Stress Faciliates Long-Lasting Changes in Cholinergic Gene Expression", Nature, 393: 373-377, 1998.

Komminoth et al. "Evaluation of Methods for Hepatitis C Virus Detection in Archival Liver Biopsies. Comparison of Histology, Immunochemistry, In-Situ Hybridization, Reverse Transcriptase Polymerase Chain Reaction (RT-PCR) and In-Situ RT-PCR", Pathology, Research and Practice, 190(11): 1017-1025, 1994.

Kondo et al. "Genetic Polymorphism of Paraoxonase 1 (PON1) and Susceptibility to Parkinson's Disease", Brain Research, 806(2): 271-273, 1998. p. 271, col. 2, Line 16-p. 272, col. 1, Line 11, p. 272, col. 1, Line 32-col. 2, Line 21.

Landegren et al. "A Ligase-Mediated Gene Detection Technique", Science, 241 (4869): 1077-1080, 1988.

Latorra et al. "Enhanced Allele-Specific PCR Discrimination in SNP Genotyping Using 3' Locked Nucleic Acid (LNA) Primers", Human Mutation, 22: 79-85, 2003.

Lerman et al. "Computational Simulation of DNA Melting and Its Application to Denaturing Gradient Gel Electrophoresis", Methods in Enzymology, 155(30): 482-501, 1987.

Leushner et al. "Automated Mass Spectrometry: A Revolutionary Technology for Clinical Diagnostics", Molecular Diagnosis, 5(4): 341-348, 2000.

Li et al. "Paraoxonase Protects Against Chlorpyrifos Toxicity in Mice", Toxicology Letters, 76: 219-226, 1995.

Liljedahl et al. "A Microarray Minisequencing System for Pharmacogenetic Profiling of Antihypertensive Drug Response", Pharmacogenetics, 13: 7-17, 2003.

Loewenstein-Lichtenstein et al. "Genetic Predisposition to Adverse Consequences of Anti-Cholinesterases in 'Atypical' BCHE Carriers", Nature Medicine, 1(10): 1082-1085, 1995.

Mackness et al. "Paraoxonase and Coronary Heart Disease", Atherosclerosis Supplements, 3: 49-55, 2002.

Maskos et al. "A Novel Method for the Parallel Analysis of Multiple Mutations in Multiple Samples", Nucleic Acids Research, 21(9): 2269-2270, 1993.

Mattila et al. "Fidelity of DNA Synthesis by the Thermococcus Litoralis DNA Polymerase—An Extremely Heat Stable Enzyme With Proofreading Activity", Nucleic Acids Research, 19(18): 4967-4973, 1991.

McGrady et al. "Effect of Repeated Measurements of Blood Pressure on Blood Pressure in Essential Hypertension: Role of Anxiety", Journal of Behavioral Medicine, 13(1): 93-101, 1990.

Meshorer et al. "Alternative Splicing and Neuritic mRNA Translocation Under Long-Term Neuronal Hypersensitivity", Science, 295(5554): 508-512, 2002.

Myers et al. "Detection of Single Base Substitutions by Ribonuclease Cleavage at Mismatches in RNA: DNA Duplexes", Science, 230: 1242-1246, 1985.

Nakamura et al. "Peripheral-Type Benzodiazepine Receptors on Platelets Are Correlated With the Degrees of Anxiety in Normal Human Subjects", Psychopharmacology, 162: 301-303, 2002.

Nemeroff et al. "Depression and Cardiac Disease", Depression and Anxiety, 8(Suppl.1): 71-79, 1998.

Neville et al. "Anionic Site Interactions in Human Butyrylcholinesterase Disrupted by Two Single Point Mutations", The Journal of Biological Chemistry, 265(34): 20735-20738, 1990.

Newton et al. "Analysis of Any Point Mutation in DNA. The Amplification Refractory Mutation System (ARMS)", Nucleic Acids Research, 17(7): 2503-2516, 1989.

Nickerson et al. "Automated DNA Diagnostics Using An ELISA-Based Oligonucleotide Ligation Assay", Proc. Natl. Acad. Sci. USA, 87: 8923-8927, 1990.

Nikiforov et al. "Genetic Bit Analysis: A Solid Phase Method for Typing Single Nucleotide Polymorphisms", Nucleic Acids Research, 22(20): 4167-4175, 1994.

Nuovo et al. "Intracellular Localization of Polymerase Chain Reaction (PCR)-Amplified Hepatitis C cDNA", The American Journal of Surgical Pathology, 17(7): 683-690, 1993.

O'Meara et al. "SNP Typing by Apyrase-Mediated Allele-Specific Primer Extension on DNA Microarrays", Nucleic Acids Research, 30(15/e75): 8 P., 2002.

Ordentlich et al. "Functional Characteristics of the Oxyanion Hole in Human Acetylcholinesterase", The Journal of Biological Chemistry, 273(31): 19509-19517, 1998.

Orita et al. "Rapid and Sensitive Detection of Point Mutations and DNA Polymorphisms Using the Polymerase Chain Reaction", Genomics, 5: 874-879, 1989.

Ørum et al. "Single Base Pair Mutation Analysis by PNA Directed PCR Clamping", Nucleic Acids Research, 21(23): 5332-5336, 1993.

Rao et al. "Genotyping Single Nucleotide Polymorphisms Directly From Genome DNA by Invasive Cleavage Reaction on Microspheres", Nucleic Acids Research, 31(11/e66): 8 P., 2003.

Ren et al. "Straightforward Detection of SNPs in Double-Stranded DNA by Using Exonuclease III/Nuclease S1/PNA System", Nucleic Acids Research, 32(4/e42): 9 P., 2004.

Rozenberg et al. "Paraoxonase (PON1) Deficiency Is Associated With Increased Macrophage Oxidative Stress: Studies in PON1-Knockout Mice", Free Redical Biology & Medicine, 34(6): 774-784, 2003.

Saiki et al. "Genetic Analysis of Amplified DNA With Immobilized Sequence-Specific Oligonucleotide Probes", Proc. Natl. Acad. Sci. USA, 86: 6230-6234, 1989.

Saiki et al. "Primer-Directed Enzymatic Amplification of DNA With A Thermostable DNA Polymerase", Science, 239(4839): 487-491, 1988.

Saito et al. "Association of Body Mass Index, Body Fat, and Weight Gain With Inflammatory Markers Among Rural Residents in Japan", Circulation Journal, 67: 323-329, 2003.

Sandberg et al. "Panic Disorder in Schizophrenia", Database BIOSIS 'Online! Biosciences Information Service, Acc. No. PREV198885031672 & Journal of Nervous and Mental Disease, 175(10): 627-628, 1987. Abstract.

Sauer et al. "Extension of the Good Assay for Genotyping Single Nucleotide Polymorphisms by Matrix-Assisted Laser Desorption/Ionization Mass Spectrometry", Rapid Communications in Mass Spectrometry, 17: 1265-1272, 2003.

Scholz et al. "Rapid Screening for Tp53 Mutations by Temperature Gradient Gel Electrophoresis: A Comparison With SSCP Analysis", Human Molecular Genetics, 2(12): 2155-2158, 1993.

Seki et al. "Effects of Phase III Cardiac Rehabilitation Programs on Health-Related Quality of Life in Elderly Patients With Coronary Artery Disease—Juntendo Cardiac Rehabilitation Program (J-CARP)", Circulation Journal, 67: 73-77, 2003.

Shapira et al. "A Transcription-Activating Polymorphism in the ACHE Promoter Associated With Acute Sensitivity to Anti-Acetylcholinesterases", Human Molecular Genetics, 9(9): 1273-1281, 2000.

Sheffield et al. "Attachment of A 40-Base-Pair G+C-Rich Sequence (GC-Clamp) to Genomic DNA Fragments by the Polymerase Chain Reaction Results in Improved Detection of Single-Base Changes", Proc. Natl. Acad. Sci. USA, 86: 232-236, 1989.

Shi "Enabling Large-Scale Pharmacogenetic Studies by High-Throughput Mutation Detection and Genotyping Technologies", Clinical Chemistry, 47(2): 164-172, 2001.

Sklan et al. "Acetylcholinesterase/Paraoxonase Genotype and Expression Predict Anxiety Scores in Health, Risks Factors, Exercise Training, and Genetics Study", Proc. Natl. Acad. Sci. USA, 101(15): 5512-5517, 2004.

Smith et al. "Novel Method of Detecting Single Base Substitutions in RNA Molecules by Differential Melting Behaviour in Solution", Genomics 3,: 217-223, 1988.

Sorensen et al. "Mormal Human Serum Contains Two Forms of Acetylcholinesterase", Clinica Chimica Acta, 158: 1-6, 1986.

Soreq et al. "Acetylcholinesterase—New Roles for An Old Actor", Nature Reviews: Neuroscience, 2: 294-302, 2001.

Suehiro et al. "A Polymorphism Upstream From the Human Paraoxonase (PON1) Gene and Its Association With PON1 Expression", Atherosclerosis, 150: 295-298, 2000.

Sussman et al. "Atomic Structure of Acetylcholinesterase From Torpedo California: A Prototypic Acetylcholine-Binding Protein", Science, 253(5022): 872-879, 1991.

Syvänen et al. "A Primer-Guided Nucleotide Incorporation Assay in the Genotyping of Apolipoprotein E", Genomics, 8: 684-692, 1990.

Thiede et al. "Simple and Sensitive Detection of Mutations in the Ras Proto-Oncogenes Using PNA-Mediated PCR Clamping", Nucleic Acids Research, 24(5): 983-984, 1996.

Tönisson et al. "Unravelling Genetic Data by Arrayed Primer Extension", Clinical Chem. Lab. Med., 38(2): 165-170, 2000.

Turner et al. "Typing of Multiple Single Nucleotide Polymorphisms in Cytokine and Receptor Genes Using SNaPshot", Human Immunology, 63: 508-513, 2002.

Vedhara et al. "An Investigation Into the relationship Between Salivary Cortisol, Stress, Anxiety and Depression", Biological Psychology, 62: 89-96, 2003.

Wagner et al. "Mutation Detection Using Immobilized Mismatch Binding Protein (MutS)", Nucleic Acids Research, 23(19): 3944-3948, 1995.

Walker et al. "Isothermal In Vitro Amplification of DNA by A Restriction Enzyme/DNA Polymerase System", Proc. Natl. Acad. Sci. USA, 89: 392-396, 1992.

Wallace et al. "Hybridization of Synthetic Oligodeoxyribonucleotides to Φx174 DNA: The Effect of Single Base Pair Mismatch", Nucleid Acids Research, 6(11): 3543-3557, 1979.

Walsh et al. "Parkinson's Disease and Anxiety", . Database BIOSIS 'Online! Biosciences Information Service, Database Acc. No. PREV200100144543 & Postgraduate Medical Journal, 77(904): 89-93, 2001. Abstract.

Wartell et al. "Detecting Base Pair Substitutions in DNA Fragments by Temperature-Gradient Gel Electrophoresis", Nucleic Acids Research, 18(9): 2699-2701, 1990.

Weiner et al. "Oxidative Stress Transforms Acetylcholinesterase to A Molten-Globule-Like State", Biochemical and Biophysical Research Communications, 198(3): 915-922, 1994.

Wolf et al. "Anticipatory Anxiety in Moderately to Highly-anxious Oral Surgery Patients as A Screening Model for Anxiolytics: Evaluation of Alprazolam", Journal of Clinical Psychopharmacology, 23(1): 51-57, 2003.

Wu et al. "The Ligation Amplification Reaction (LAR)—Amplification of Specific DNA Sequences Using Sequential Rounds to Template-Dependent Ligation", Genomics, 4: 560-569, 1989.

Youil et al. "Screening for Mutations by Enzyme Mismatch Cleavage With T4 Endonuclease VII", Proc. Natl. Acad. Sci. USA, 92: 87-91, 1995.

Zakut et al. "Modified Properties of Serum Cholinesterases in Primary Carcinomas", Cancer, 61: 727-737, 1988.

* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gtgagaatgg ctgcttcata                                                     20

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
ctcagttctg ggaaattcct a                                                   21

<210> SEQ ID NO 3
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 3
cgggtctacg cctacgtctt tgaacaccgt gcttc                                    35

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4 cccgtcettt ctgtctcgtg tg                                                  22

<210> SEQ ID NO 5
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 5
cttggtagac ttcgattcaa aaagccacag tct                                      33
```

```
<210> SEQ ID NO 6
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 6
gaatccatac atttagatat aaacagtctt cactg                              35

<210> SEQ ID NO 7
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 7
actgaatctc tctgagacgc aaggacc                                       27

<210> SEQ ID NO 8
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 8
atagacaaag ggatcgatgg gcgcagaca                                     29

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
gaagagtgat gtatagcccc ag                                            22

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 10
acactcacag agctaatgaa agcc                                          24

<210> SEQ ID NO 11
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 11
ggaatagaca gtgaggaatg ccagt                                         25

<210> SEQ ID NO 12
<211> LENGTH: 26
<212> TYPE: DNA
<213> ORGANISM: Artificial sequence
<220> FEATURE:
<223> OTHER INFORMATION: Single strand DNA oligonucleotide
```

```
<400> SEQUENCE: 12
cagagagttc acatacttgc catcgg                                          26

<210> SEQ ID NO 13
<211> LENGTH: 22
<212> TYPE: DNA
<213> ORGANISM: Artificial sequence
<220> FEATURE:
<223> OTHER INFORMATION: Single strand DNA probe

<400> SEQUENCE: 13
ggcagaaact ggctctgaag ac                                              22

<210> SEQ ID NO 14
<211> LENGTH: 28
<212> TYPE: DNA
<213> ORGANISM: Artificial sequence
<220> FEATURE:
<223> OTHER INFORMATION: Single strand DNA probe

<400> SEQUENCE: 14
gatcactatt ttcttgaccc ctacttac                                        28

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
gtagatggag acttcctcag tg                                              22

<210> SEQ ID NO 16
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 16
agagatgaac agttacagac cc                                              22
1
```

METHOD FOR ASSESSING TRAIT ANXIETY BY DETERMINING CHOLINERGIC STATUS

RELATED APPLICATIONS

This application is a continuation-in-part of PCT/IL2004/000933, filed on Oct. 10, 2004, which claims the benefit of U.S. Provisional Patent Application No. 60/510,560, filed on Oct. 10, 2003, the contents of which, including the contents of the CD-ROMs submitted therewith, are incorporated by reference as if fully set forth herein.

STATEMENT OF GOVERNMENT SUPPORT

This work was supported by the US Army Medical Research and Material Command (DAMD 17-99-1-9547) and the Defense Advance Research Project Agency (#N66001-01-C-8015). The U.S. government has certain rights in this invention.

FIELD AND BACKGROUND OF THE INVENTION

The present invention relates to a method and kit for assessing anxiety or anxiety disposition in a subject and, more particularly, to methods for qualifying ChE and PON expression levels and in particular the relationship therebetween, which methods enable assessment of anxiety.

Anxiety involves complex, incompletely understood interactions of genomic, environmental and experience-derived factors and is currently being measured by psychological criteria. Anxiety is a ubiquitous and unavoidable experience of life, and is defined as a feeling of fear that is out of proportion to the nature of the threat. Anxiety disorders are reported to be the most prevalent of psychiatric disorders.

Anxiety, or susceptibly to anxiety, is typically assessed by evaluating responses from subjects to specific questions relating to danger and stress. For example, the two 20-item self-report questionnaires of the state-trait anxiety inventory (STAI) are commonly used to measure anxiety. STAI scores increase in response to physical danger and psychological stress or in neurotic and depressed subjects, and decrease as a result of relaxation training.

While reducing the present invention to practice, the present inventor has correlated between expression levels of AChE/BChE and PON and in particular an expression ratio therebetween and predisposition to anxiety or early state of anxiety.

Thus, the present invention enables for the first time biochemical or molecular diagnosis of Anxiety.

SUMMARY OF THE INVENTION

The invention is based in part on the discovery that genomic polymorphisms in the acetylcholinesterase (ACHE) and the paraoxonase (PON1) genes (also known as the ACHE-PON1 locus) and corresponding changes in serum AChE and PON activities can serve as objective predictors of anxiety in human subjects.

Accordingly, in one aspect, the invention features a method of assessing trait anxiety in a subject. The method includes providing from the subject a test sample, which can be any biological fluid, cell sample, or tissue, as long as it contains genomic DNA from the subject, and/or RNA transcribed from the ACHE, PON1, or BCHE genes. The test sample is assayed to determine whether it contains a polymorphism in an acetylcholinesterase (ACHE) gene, a paraoxonase (PON1) gene, and/or a butyrylcholinesterase (BCHE), which is associated with a known level of trait anxiety, e.g., whether it is associated with a specific trait anxiety score. The presence of the polymorphism in the sample indicates the subject has the corresponding level of anxiety.

In some embodiments, the subject is a human. In other embodiments, the subject is a non-human primate, dog, cat, cow, horse, pig, goat, sheep, or rodent (including a rat or mouse), or other mammal.

In some embodiments, the polymorphism is compared to the polymorphism in a reference sample derived from one or more individuals whose trait anxiety level is known, to assess trait anxiety in the subject.

In some embodiments, the subject is a human (including a healthy human or a diseased human). In some embodiments, polymorphisms are identified in humans that are members of certain racial or ethnic groups, e.g., Caucasians, Blacks, Asians, or Hispanics.

Suitable ACHE gene polymorphisms include, e.g., the 1682 C/T (P446) ACHE polymorphism in a human ACHE gene.

Suitable PON1 gene polymorphisms include, e.g., a polymorphism in a PON1 gene promoter polymorphism. PON1 promoter polymorphisms can include, e.g., −162A/G PON1, −126 G/C PON1, or −108 C/T PON1 substitutions in a human PON1 gene.

Alternatively, the PON1 polymorphism can be in a PON1 coding sequence. PON1 coding sequence polymorphisms can include, e.g., a polymorphism that results in a L55M or Q192R substitution in a human PON1 coding sequence.

In some embodiments, the BCHE polymorphism results in a D70G substitution in a human BCHE coding sequence.

In some embodiments, the method includes identifying and comparing at least two polymorphic pairs in the ACHE, PON1, and/or BCHE genes. Suitable polymorphic pairs include, e.g., ACHE P446 and PON1108; ACHE P446 and PON1192; PON1108 and PON1126; or PON1126 and PON1162.

In another aspect, the invention provides a method of assessing trait anxiety in a subject. The method includes providing a test sample from the subject and identifying acetylcholinesterase (AChE) activity in the test sample. AChE activity in the test sample is compared to AChE activity in a reference sample derived from one or more individuals whose trait anxiety level is known. The individual or individuals in the reference sample are similar to the subject in at least one or more of the traits gender, age, race, ethnic group, and body mass index. In some embodiments, the subject and individual or individuals are similar in two, three, four or five of these traits. In some embodiments, AChE activity in the test sample is compared to an average AChE activity in the individual or individuals in the reference sample. A higher level of AChE activity in the test sample compared to AChE activity in the reference sample indicates the subject has less trait anxiety than the trait anxiety level of the one or more individuals from which the reference sample was derived.

Any biological fluid, cell sample, or tissue can be used in the test sample, as long as it contains, or is suspected of containing active AChE protein. A preferred test sample includes serum.

In some embodiments, the subject is a human (including a healthy human or a diseased human). In some embodiments, polymorphisms are identified in humans that are members of certain racial or ethnic groups, e.g., Caucasians, Blacks, Asians or Hispanics.

Also within the invention is a method of assessing trait anxiety in a subject. The method includes providing a test sample from the subject and identifying acetylcholinesterase (AChE) monomeric forms in the test sample. The amount of AChE monomeric forms in the test sample is compared to the amount of AChE monomeric forms in a reference sample derived from one or more individuals whose trait anxiety level is known in order to assess trait anxiety in the subject. A higher amount of AChE monomeric forms in the test sample compared to AChE monomeric forms in the reference sample indicates the subject has less trait anxiety than the trait anxiety level of the one or more individuals from which the reference sample was derived.

In some embodiments, the AChE monomeric forms are detected using non-denaturing gel electrophoresis.

Any biological fluid, cell sample, or tissue can be used in the test sample, as long as it contains, or is suspected of containing AChE monomeric forms. A preferred test sample is serum.

In some embodiments, the subject is a human (including a healthy human or a diseased human). In some embodiments, polymorphisms are identified in humans that are- members-of-certain racial or ethnic groups, e.g., Caucasians, Blacks, Asians, or Hispanics.

The individual or individuals in the reference sample are similar to the subject in at least one or more of the traits gender, age, race, ethnic group, and body mass index. In some embodiments, the subject and individual or individuals are similar in two, three, four or five of these traits.

Also featured by the invention is a method of determining susceptibility to state anxiety in a subject. The method includes providing a test sample from the subject and identifying PON activity in the subject. PON activity in the test sample is compared to the amount of PON activity in a reference sample derived from one or more individuals whose state anxiety level is known.

In some embodiments, lower PON activity in the test sample relative to the reference sample indicates the subject is at increased susceptibility for developing state anxiety than the one or more individuals in the reference sample.

The individual or individuals in the reference sample are similar to the subject in at least one trait selected from the traits gender, age, race, ethnic group, and body mass index. In some embodiments, the subject and individual or individuals are similar in two, three, four or five of these traits.

In some embodiments, the method includes identifying AChE activity in the subject and comparing the AChE activity to AChE activity in the one or more individuals.

In some embodiments, the subject is a human (including a healthy human or a diseased human). In some embodiments, polymorphisms are identified in humans that are members of certain racial or ethnic groups, e.g., Caucasians, Blacks, or Hispanics. Any biological fluid, cell sample, or tissue can be used in the test sample, as long as it contains, or is suspected of containing AChE monomeric forms. A preferred test sample is serum.

In a further aspect, the invention provides a method of determining susceptibility to state anxiety in a subject by providing a test sample from the subject and identifying AChE activity in the test sample. AChE activity in the test sample is compared to the amount of AChE activity in a reference sample derived from one or more individuals whose state anxiety level is known. The individual or individuals in the reference sample are similar to the subject in one or more of the traits gender, age, race, ethnic group, or body mass index. In some embodiments, the subject and individual or individuals are similar in two, three, four or five of these traits.

In some embodiments, a higher level of AChE in the test sample compared to the reference sample indicates the subject has increased susceptibility to state anxiety compared to the one or more individuals in the reference sample.

In a further aspect, the invention provides a method of assessing state anxiety in a subject. The method includes providing a plurality of test samples, with the test samples taken from the subject at different times. PON activity is identified in the plurality of test samples and the PON activity of two or more test samples from the plurality of test samples is compared.

In some embodiments, comparing PON activity includes comparing PON activity of one or more test samples taken at one or more timepoints before administering an anxiety treatment and one or more test samples taken at one or more timepoints after administering an anxiety treatment. In other embodiments, comparing PON activity includes comparing PON activity of one or more test samples taken at one or more timepoints during an anxiety attack and one or more test samples taken at one or more timepoints after an anxiety attack.

In another aspect, the invention provides a method of assessing state anxiety in a subject including providing a plurality of test samples from the subject taken at different times from the subject. AChE activity in the plurality of test samples is identified and AChE activity of two or more test samples from the plurality of test samples is compared.

In some embodiments, comparing AChE activity includes comparing AChE activity of one or more test samples taken at one or more timepoints before administering an anxiety treatment and one or more test samples taken at one or more timepoints after administering anxiety treatment. In other embodiments, comparing AChE activity includes comparing AChE activity of one or more test samples taken at one or more timepoints during an anxiety attack and one or more test samples taken at one or more timepoints after an anxiety attack.

The anxiety can be either a primary, non-situational anxiety, or a secondary, situational anxiety. In some embodiments, the situational anxiety can be depression-related anxiety or hypertension related anxiety.

In another aspect, the invention provides a method for monitoring treatment outcome of an anti-anxiety therapy in a subject, comprising comparing cholinergic enzyme activity of one or more test samples taken at one or more timepoints before administering an anxiety treatment and one or more test samples taken at one or more time points after administering anxiety treatment.

In another embodiment, monitoring changes in cholinergic enzymes in depression-related anxiety is used for monitoring treatment outcome of an anti-depression therapy in a subject, comprising comparing cholinergic enzyme activity of one or more test samples taken at one or more timepoints before administering an anti-depression treatment and one or more test samples taken at one or more timepoints after administering anti-depression treatment.

Also provided are kits for monitoring treatment outcome of an anti-anxiety therapy in a subject, comprising reagents for determining in a biological sample of the subject activity levels of at least one of cholinesterase (ChE) and/or paraoxonase (PON1). In some embodiments, the kits further comprise means for comparing between the activity levels at different time points.

Also provided are kits for monitoring treatment outcome of an anti-depression therapy in a subject, comprising reagents for determining in a biological sample of the subject activity levels of at least one of cholinesterase (ChE) and/or paraoxonase (PON1). In some embodiments, the kits further comprise means for comparing between the activity levels at different time points.

Further, the invention provides for kits for assessing trait or state anxiety in a subject, the kits comprising reagents for determining in a biological sample of the subject activity levels of at least one of cholinesterase (ChE) and/or paraoxonase (PON1). In some embodiments, the kits further comprise means for comparing between the activity levels of the at least one of cholinesterase and/or said paraoxonase and a reference standard of known levels of at least one of cholinesterase (ChE) and/or paraoxonase (PON1) activity.

The present invention successfully addresses the shortcomings of the presently known configurations by providing a biomolecular or biochemical diagnostic tool which enables accurate and rapid diagnosis of subjects afflicted with anxiety or being predisposed thereto.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic diagram showing chromosome positions and polymorphic sites in the ACHE (AF002993), BCHE (NM_000055) and PON1 (AF539592) genes. Nucleotide numbers begin at the transcription start site at 0;

FIG. 2 is a graph showing changes in anxiety levels and levels of AChE, BChE, and paraoxonase as a function of age or body mass index (BMI). Graphs show mean ±SEM of each group (n=434);

FIG. 3 is a graph showing serum ACHE activity, cortisol levels, BChE, and PON levels as a function of trait anxiety;

FIG. 4 is an electrophoretogram showing AChE-R tetrameric, dimer, and monomer forms in serum of subjects with high or low trait anxiety;

FIG. 5 is a prediction tree based on age, gender, AChE, BChE and PON activities;

FIG. 6 is a contour map showing the inter-related consequences of AChE and PON variations on state anxiety;

FIG. 7A is a graph of plasma enzyme activities, normalized to the population average, for AChE, arylesterase, BChE and paraoxonase;

FIG. 7B is graphs of AChE, paraoxonase, BChE and arylesterase plasma enzyme activities plotted against age;

FIG. 8A is a histogram of paraoxonase and arylesterase enzyme activates for each PON1-108/55 haplotype;

FIG. 8B is a depiction of superimposed structures of PON1 55L and PON1 55M, with a magnified view showing position 55 and two neighboring amino acids that coordinate two calcium atoms;

FIG. 9 is a graph of arylesterase activity in PON1 55L (n=39), LM (n=38) and MM (n=14) individuals subclassified into age groups;

Figure 10A:
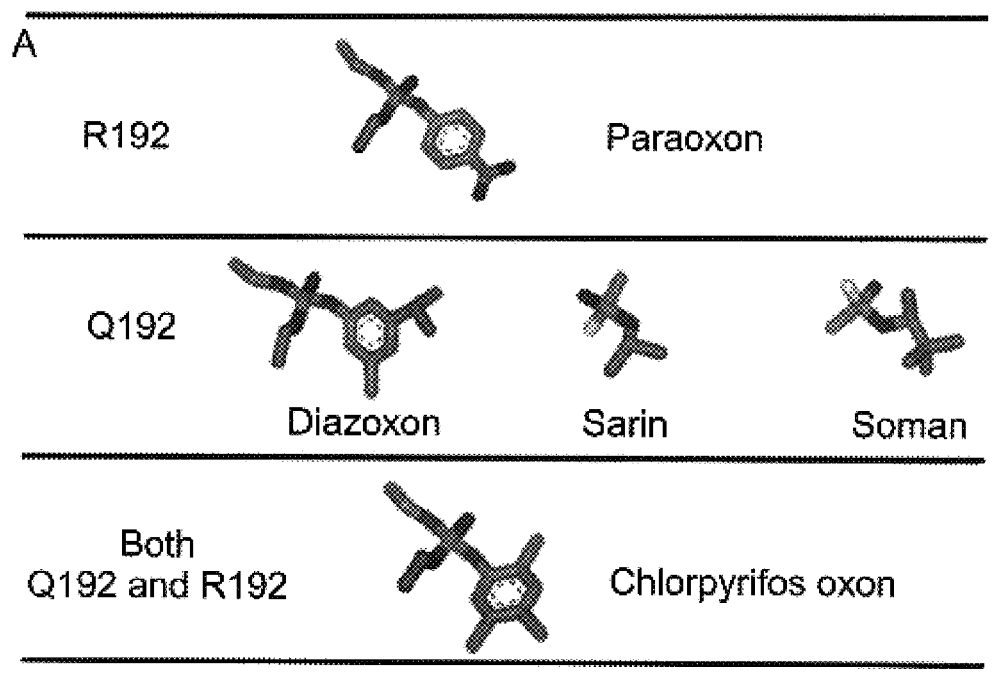
Figure 10B:
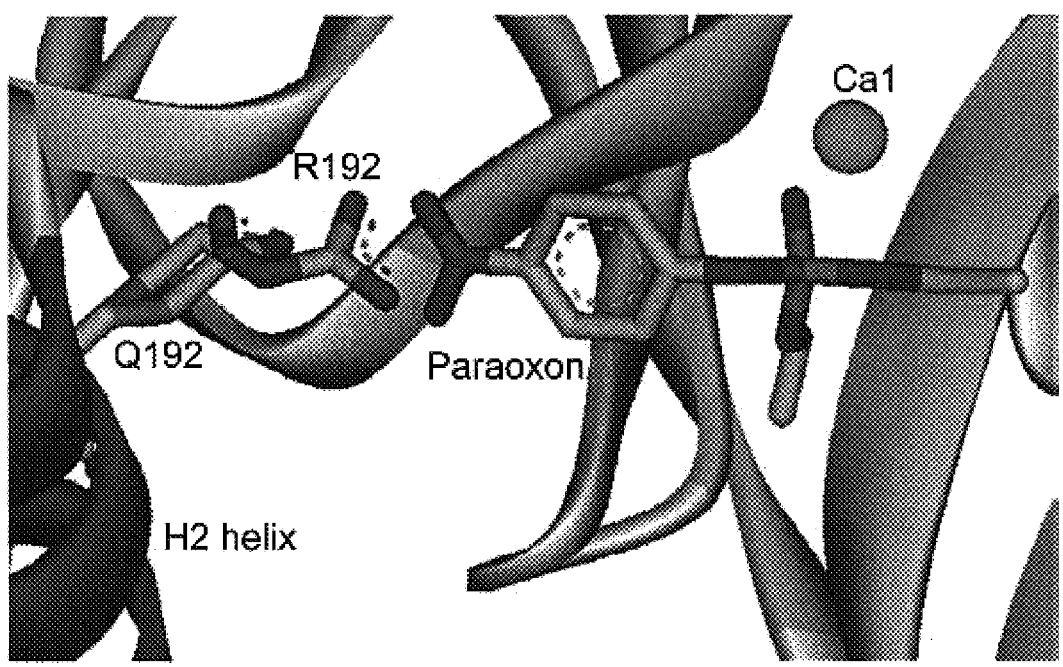
Figure 10C:
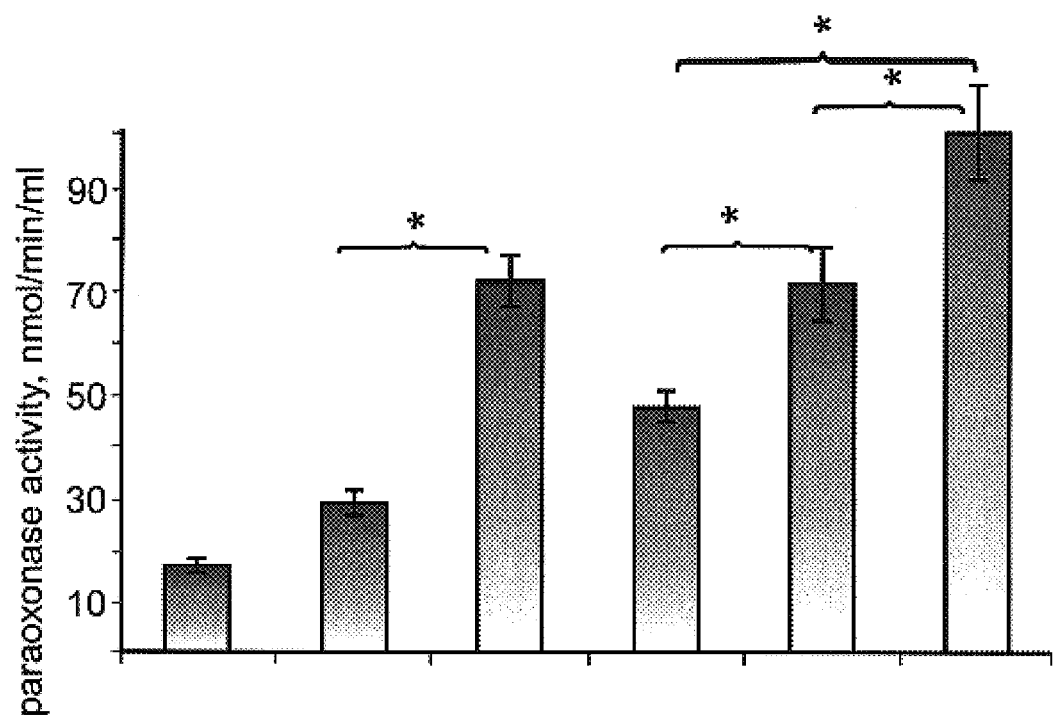
Figure 11A:
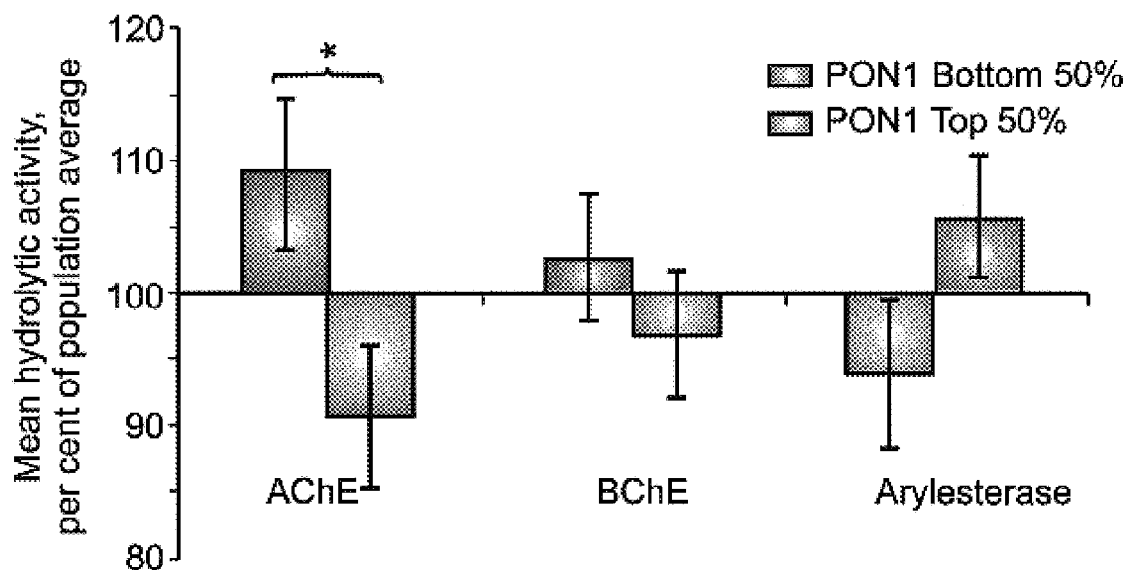
Figure 11B:
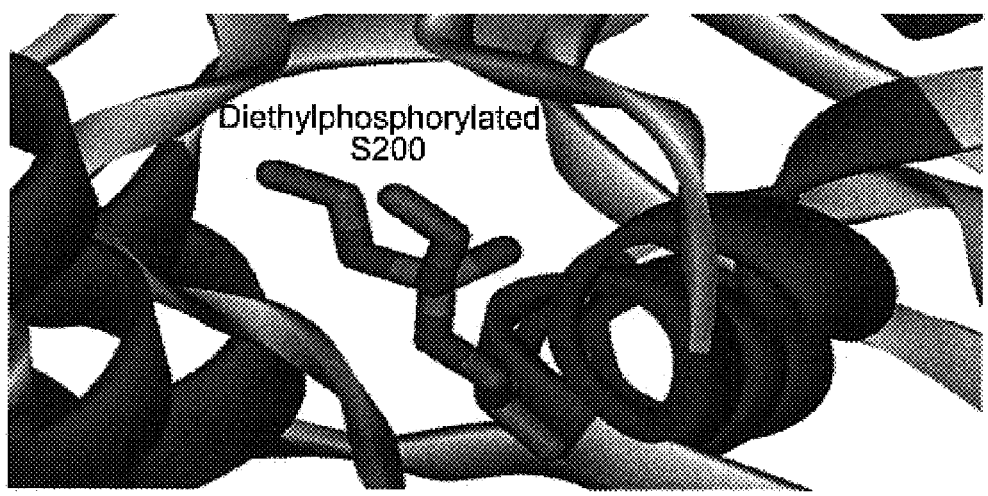
Figure 11C:
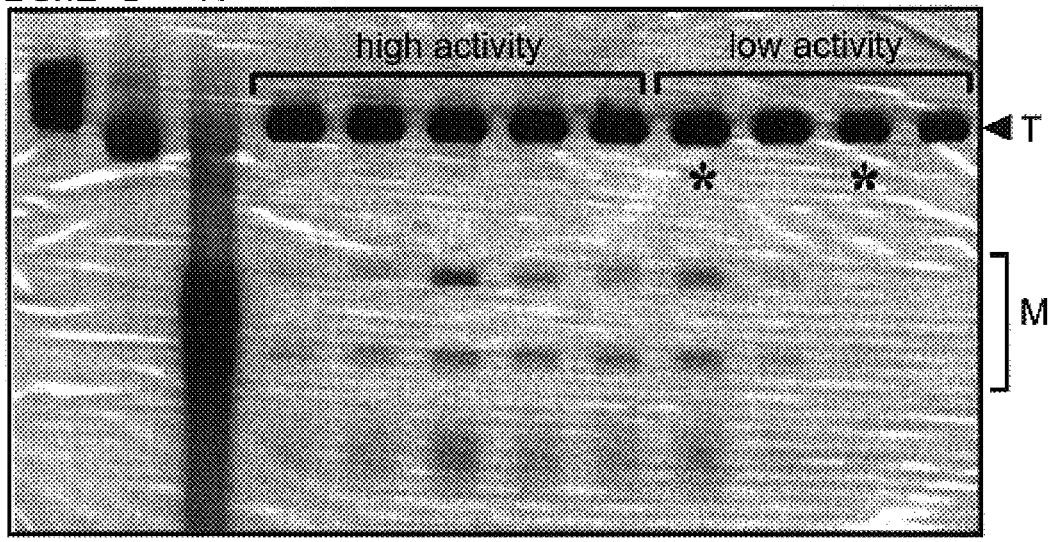
Figure 12:
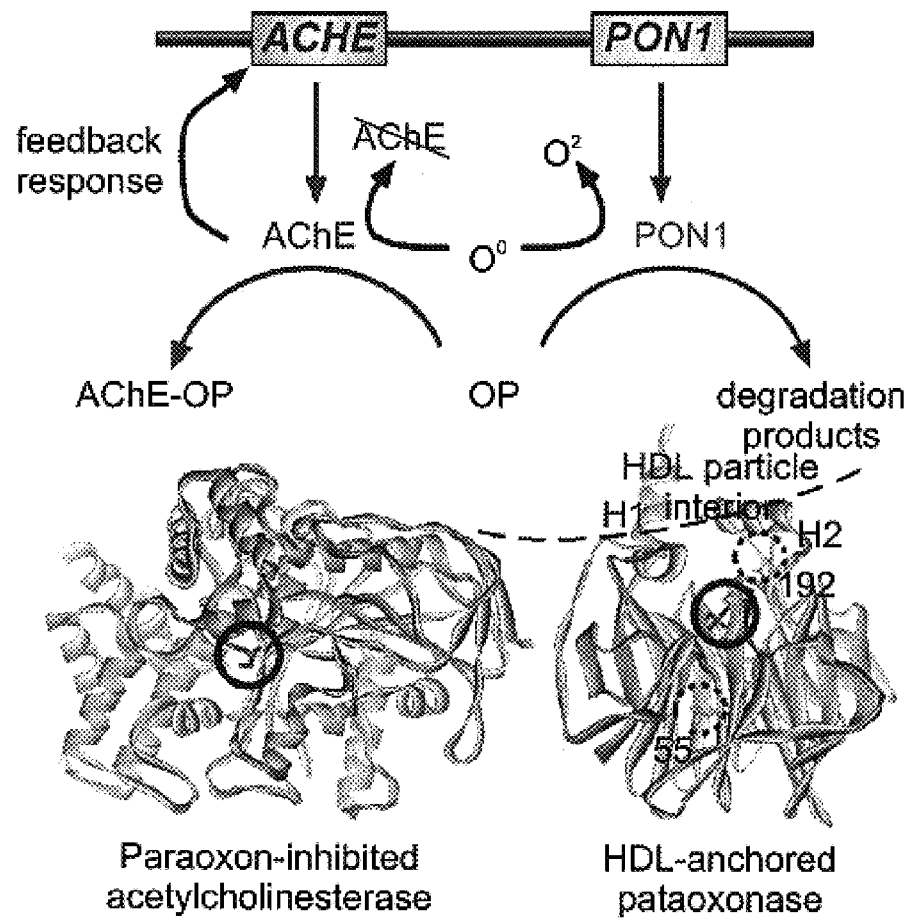
Figure 13A:
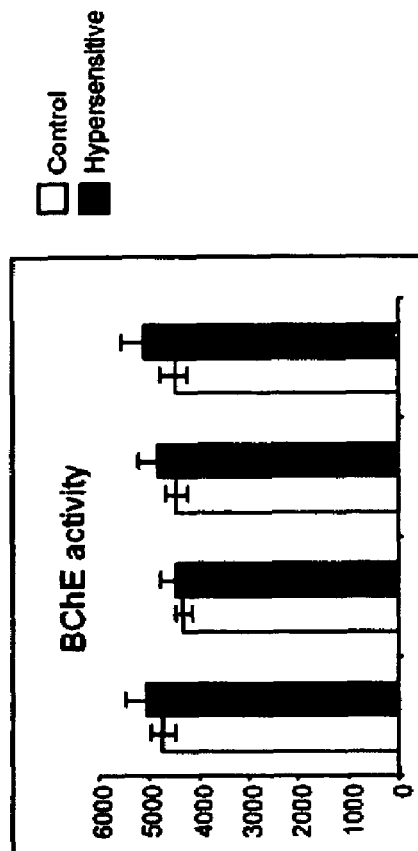
Figure 13B:
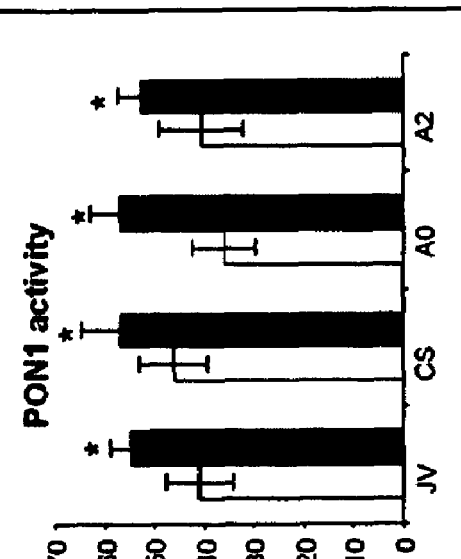
Figure 13C:
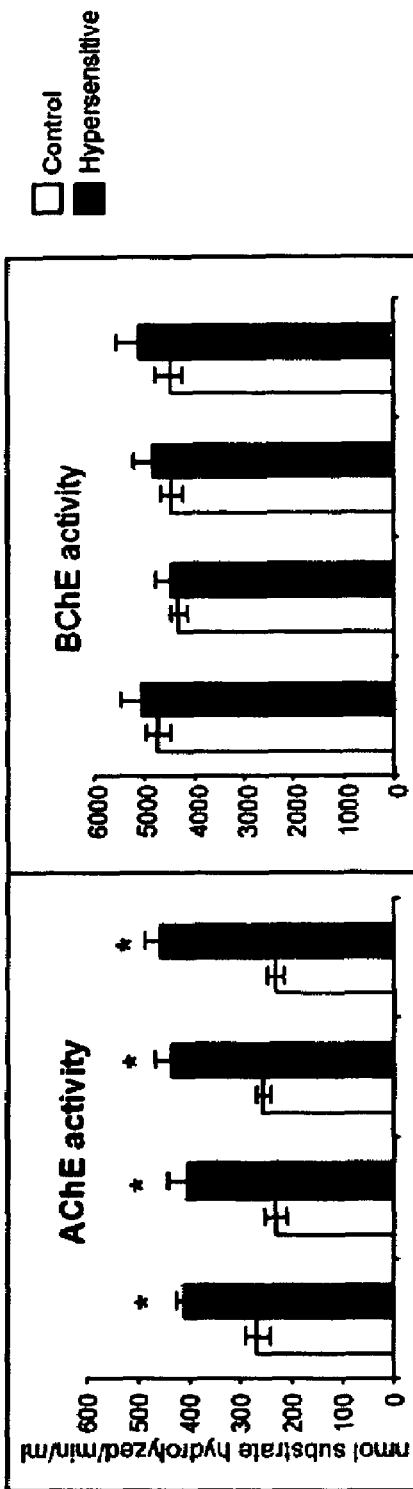
Figure 13D:
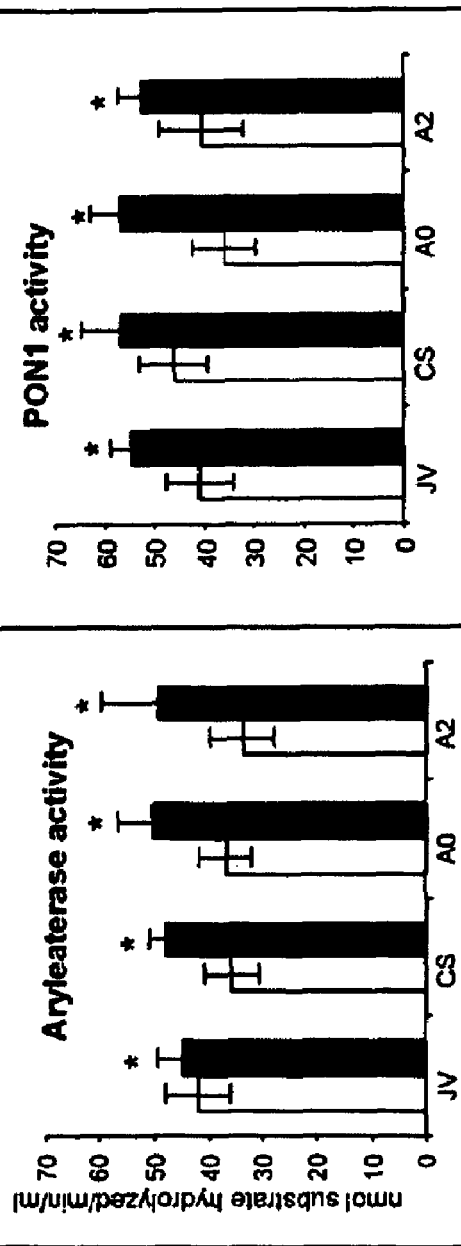
Figure 14A:
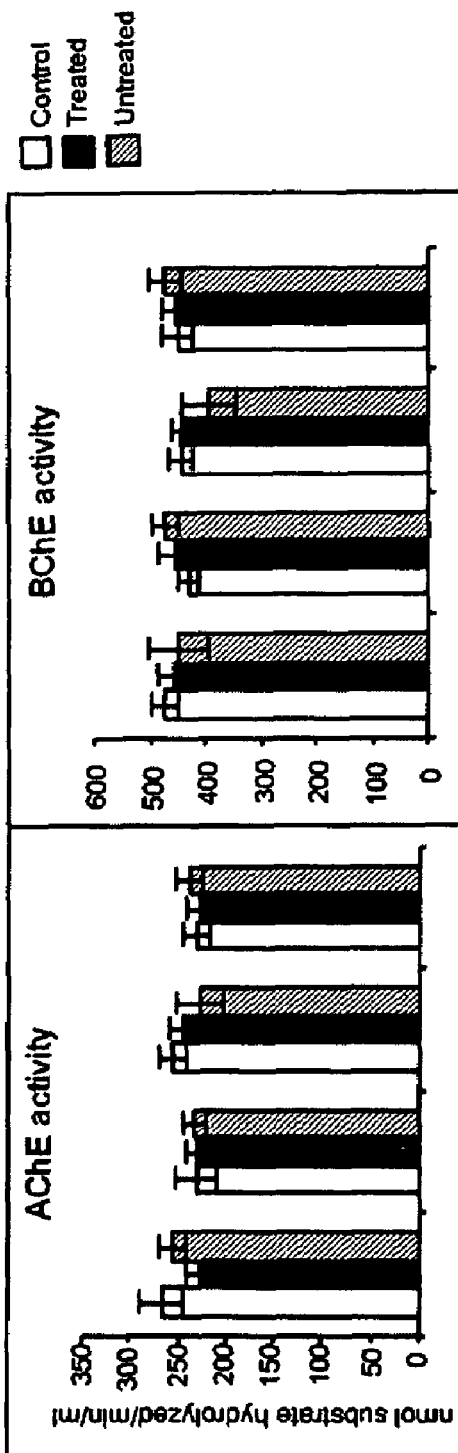
Figure 14B:
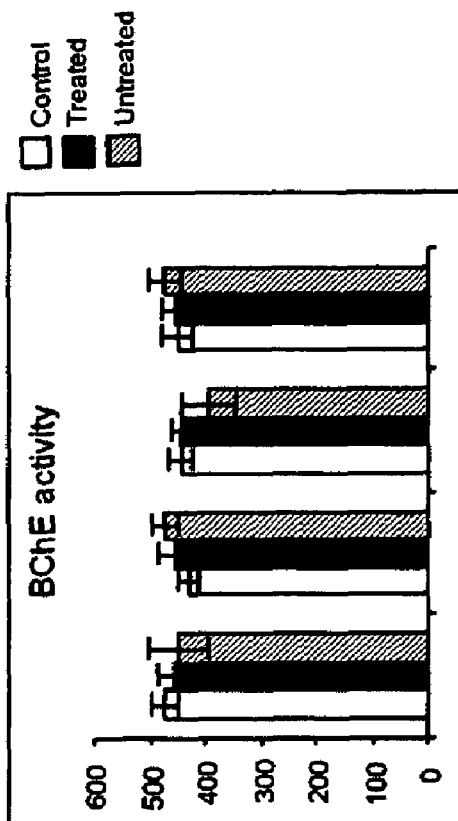
Figure 14C:
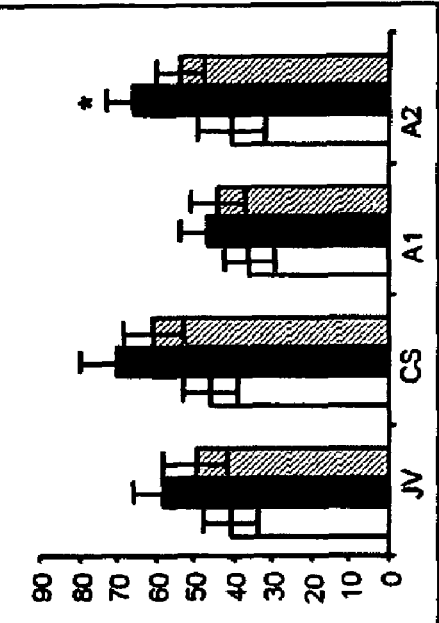
Figure 14D:
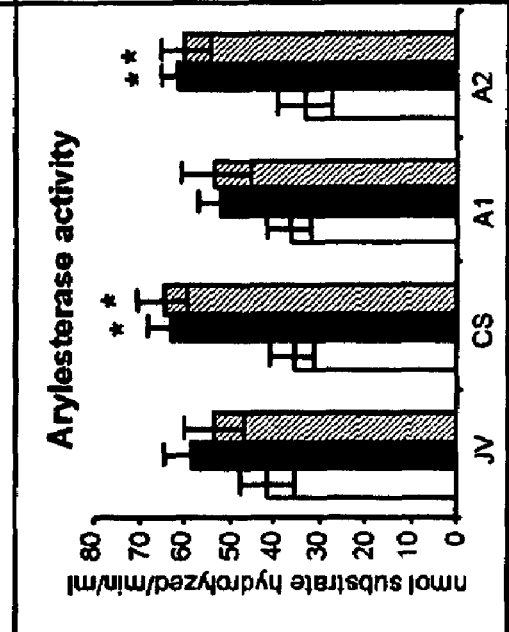
Figure 15:
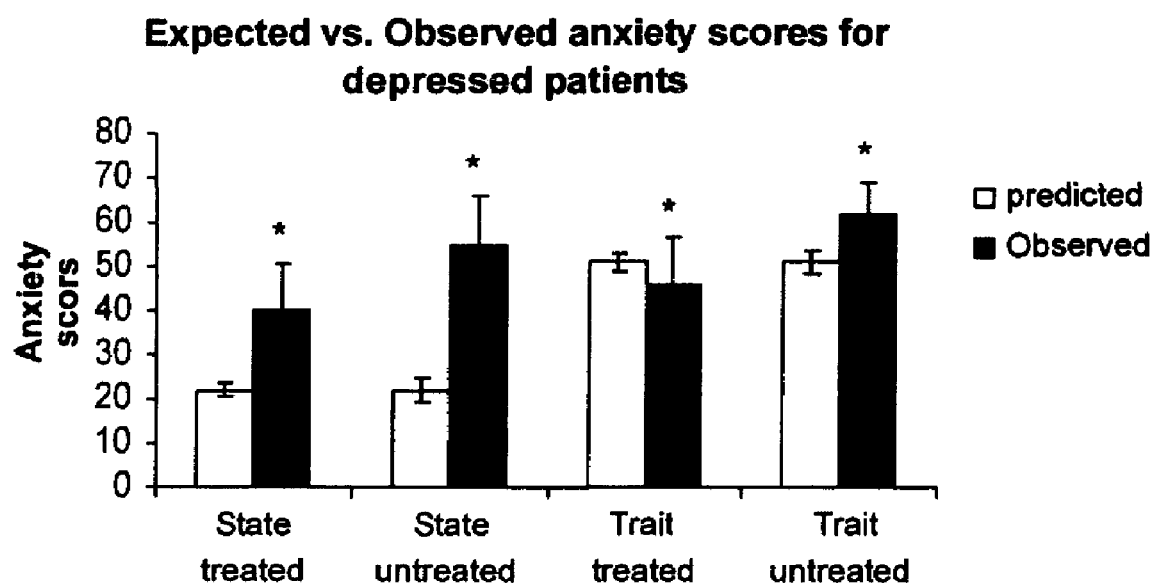

FIG. 10A is a depiction of the structures of some typical OP substrates, with the top showing substrates better hydrolyzed by R192, the middle showing substrates better hydrolyzed by Q192, and the bottom showing substrates hydrolyzed equally well by both alloenzymes;

FIG. 10B is a depiction of paraoxon docked in the active site of PON1, with the arginine and glutamine residues at position 192 superimposed;

FIG. 10C is a histogram of paraoxonase activities in different PON1 55/192 genotype groups;

FIG. 11A is a histogram of enzyme activity for AChE, BChE and arylesterase activity in individuals in the bottom 50% and the top 50% of paraoxonase activity;

FIG. 11B is a depiction of diethylphosphorylated-AChE conjugate resulting from paraoxon reaction with Ser200 in the active site gorge of AChE;

FIG. 11C is a picture of a non-denaturing polyacrylamide gel stained for catalytic activity and containing plasma samples from subjects with high and low AChE activity;

FIG. 12 is a depiction of the mechanisms of interaction between AChE and PON1 at the protein level;

FIGS. 13A-13D are histograms illustrating the correlation between hypertension and serum cholinergic activity. Serum AChE (FIG. 13A), BChE (FIG. 13B), arylesterase (FIG. 13C) and PON1 (FIG. 13D) activity was assayed in blood samples from the jugular vein (JV), carotid sinus (CS), and two (2) aortic samples (A0 and A2) from six (6) hypertensive subjects (filled bars) and four (4) matched, normotensive controls (open bars). Note the consistent differences in AChE, PON1 and arylesterase, but not BChE, activity, between the hypertensive and normotensive subjects;

FIGS. 14A-14D are histograms illustrating the effects of SSRI treatment on serum cholinergic activity in depressed patients. Serum AChE (FIG. 14A), BChE (FIG. 14B), arylesterase (FIG. 14C) and PON1 (FIG. 14D) activity was assayed in blood samples from the jugular vein (JV), carotid sinus (CS), and two (2) aortic samples (A1 and A2) from fourteen (14) treated (filled bars) and untreated (hatched bars) depressed and five (5) normal controls (open bars). Note the consistently elevated arylesterase activity in AChE activity, between the depressed and normal subjects; and FIG. 15 is a histogram illustrating the accurate prediction using the Sklan equation of Trait and State anxiety scores in treated and untreated depressed subjects. The Sklan equation was used to predict State- and Trait anxiety scores in 14 depressed patients before and following treatment. Predicted scores (open bars) correlated well with the observed values (filled bars) in the Trait-anxiety, but not State-anxiety groups, supporting the notion of disease-associated anxiety which has been successfully ameliorated by the employed treatment.

DESCRIPTION OF THE PREFERRED EMBODIMENTS

The present invention is of a method which can be utilized to quickly and accurately asses an anxiety state or predisposition in a subject. Specifically, the present invention can be used to diagnose anxiety in a subject using highly accurate commonly used biochemical and/or molecular techniques.

The invention provides methods for assessing levels of trait or state anxiety in a subject by comparing genotypes and/or expression patterns at the ACHE, PON1 and/or BChE genes to the genotype and/or expression pattern of the genes in a reference population whose genotype and/or expression pattern of the genes is known.

The term "state anxiety" refers to anxiety that is experienced by an individual at a certain time. The term "trait anxiety" refers to a general susceptibility to anxiety in an individual. Anxiety disorders include, but are not limited to, panic attack, agoraphobia, panic disorder without agoraphobia, panic disorder with agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance induced anxiety disorder, separation anxiety disorder, sexual aversion disorder and anxiety disorder not otherwise specified. See Diagnostic and Statistical Manual for Mental Disorders, $4^{th}$ Ed (1994) pp. 393-444.

The physiological manifestations that accompany anxiety may include intense fear, racing heart, turning red or blushing, excessive sweating, dry throat and mouth, trembling, swallowing with difficulty, and muscle twitches. The psychological manifestations may include feelings of impending danger, powerlessness, apprehension and tension. Commonly used indices of anxiety include the STAI, ASQ, Cornell, and compound indices (for assessment of anxiety and related conditions) such as the DASS (Depression, Anxiety Stress Scale).

It will be appreciated that anxiety is an important component of many normal behaviors, such as fright, physical pain or trauma, etc. As an adaptive behavior, an appropriate level of anxiety in such instances can serve a constructive purpose. However, abnormal or misdirected anxiety, inappropriate relative to the severity of the circumstance, is counterproductive, and may become a disorder in and of itself. A chronically recurring case of anxiety that has a serious affect on your life may be clinically diagnosed as an anxiety disorder. The most common anxiety disorders are Generalized anxiety disorder, Panic disorder, Social anxiety disorder, phobias, Obsessive-compulsive disorder, and posttraumatic stress disorder (PTSD). Thus, one may distinguish between situational anxiety, secondary to pain, another underlying medical condition, a hormone-secreting tumor, or a side effect of medication or other primary factors, and the pathological, primary non-situational anxiety unrelated to disease, disorder, etc.

The term "non-situational anxiety" refers to anxiety that does not stem from, or does not occur simultaneously with (associated) another physiological or psychological disorder or disease.

The term "situational anxiety" refers to anxiety that does stem from, or does not occur simultaneously with (associated) another physiological or psychological disorder or disease.

A non-limiting list of conditions and factors which can provoke such secondary anxiety includes poorly controlled pain; abnormal metabolic states such as hypoxia, pulmonary embolus, sepsis, delirium, hypoglycemia, bleeding coronary occlusion, heart failure and electrolyte imbalance; endocrine disorders such as hyperthyroidism and pheochromocytoma; and use of anxiety producing drugs, such as corticosteroids, thyroxine, bronchodilators, beta-adrenergic stimulants and antihistamines.

While reducing the present invention to practice, it was uncovered that genotypes and/or expression patterns of genes encoding cholinergic enzymes, such as AChE, BChE, arylesterase and PON1, are correlated with levels of anxiety in both primary, non-disease-related and secondary, disease-related anxiety.

The ACHE, PON1 and/or BCHE genes encode polypeptides involved in neurotransmission mediated by the neurotransmitter acetylcholine (ACh). ACh contributes to numerous physiologic functions, including motor activity and secretion processes as well as cognition and behavioral states, including memory, learning and panic responses. Anxiety is known to provoke cholinergic hyper-arousal (e.g. sweating, intestinal or gastric constrictions etc.). In addition, AChE is a target of pesticides and human exposure to them, or to the closely related chemical warfare agents, depletes the catalytic activity of both AChE and the homologous enzyme butyrylcholinesterase (BChE).

While not wishing to be bound by theory, the invention described herein was developed in part by investigating the hypothesis that anxiety trait scores reflect inherited genotype properties combined with the corresponding enzyme activities, as affected by demographic parameters. It was also postulated that the capacity to respond to changing conditions by increasing serum AChE levels would be more limited in subjects with high basal activity of serum AChE, because there is a maximal expression level for this gene that is likely independent of demographic parameters. PON activity may determine the requirement for AChE overproduction. Therefore, the prediction of state anxiety was tested for association with the difference between the observed and predicted activity values of AChE and PON.

Measurements of serum AChE-PON enzyme activities were performed in samples from 451 healthy subjects participating in the HERITAGE Family Study. The HERITAGE Family Study was originally designed to evaluate the role of genetic and non-genetic factors in cardiovascular, metabolic, and hormonal responses to aerobic exercise training. For a description of the study, see Bouchard et al. *Medicine and Science in Sports and Exercise* 27:721-29, 1995.

Measurements of serum AChE-PON enzyme activities, when corrected for demographic parameters, revealed interrelated inverse associations with state anxiety scores, supporting the notion of corresponding enzyme relationships. These results indicate that a significant source of anxiety feelings involves inherited and acquired parameters of acetylcholine regulation that can be readily quantified, providing an independent tool for assessing anxiety measures. The findings reveal previously non-perceived interrelationships between anxiety feelings, serum AChE, BChE and PON activities, and their corresponding genotypes.

While not wishing to be bound by theory, it is postulated that polymorphisms in the corresponding ACHE and BCHE genes can affect both the environmental and the experience-related elements of anxiety. Furthermore, the paraoxonase PON1 gene is adjacent to the AChE gene, ACHE on chromosome 7. Also, the PON1 protein product can affect AChE activity by destroying environmental toxins that target AChE.

Polymorphisms in the ACHE, BCHE and PON1 genes therefore affect both the environmental and the experience-related elements of anxiety.

Assessing Anxiety by Identifying ACHE-PON1 and/or BCHE Polymorphisms

Trait anxiety is assessed by determining whether a test sample from a subject contains a polymorphic form of a ACHE, PON1 and/or BCHE gene that is associated with a particular level of anxiety (trait or state). For example, the polymorphism can be associated with a particular anxiety score or scoring range in the STAI index. In general, any polymorphism in an ACHE, PON1, and/or BCHE gene that correlates with a particular level of trait or state anxiety can be used.

ACHE polymorphisms include promoter and coding sequence polymorphisms. The extended human ACHE promoter includes a functional glucocorticoid response element (GRE). In one ACHE1 polymorphism, a region of this element is deleted (Shapira et al., Hum. Mol. Genet. 9:1273-81, 2000). A second polymorphism in the AChE gene is the P446-polymorphism (Bartels et al. Am. J. Hu. Genet. 52:928-36, 1993).

Suitable PON1 promoter polymorphisms include (indicated by the distance in nucleotides from the transcription start site at 0): −108 C/T, which contributes to 22.4% of the variation in PON1 expression, possibly by eliminating a potential SP1 transcription factor binding site (Suehiro et al., Atherosclerosis 150:295-98, 2000); −162 G/C, which contributes to 2.4% of this variation (Brophy et al., Am. J. Human Genet. 68:1428-36, 2001) and −126 C/G (Costa et al. Ann. Rev Med 54:371-92, 2003). Suitable polymorphisms in the PON1 coding region include those changing the encoded polypeptide sequence, e.g., the PON1 polymorphisms can include (indicated by amino acid number and symbol) L55M (CTG into ATG) (Garin et al., J. Clin. Invest. 99:62-66, 1997) and Q192R (CAA into CGA) (Davies et al., Nat. Genet. 14:334-36, 1996).

Suitable BCHE polymorphisms include the D70G (Neville et al., J. Biol. Chem. 265:20735-38, 1990).

The test sample can be any biological fluid, cell sample, or tissue, as long as it contains genomic DNA from the subject, and/or RNA transcribed from the ACHE, PON1, or BCHE genes. Thus, a suitable test sample includes one obtained from any nucleated cell of the body, such as those present in peripheral blood, urine, saliva, buccal samples, surgical specimen, and autopsy specimens.

Methods of preparing nucleic acids in a form that is suitable for mutation detection is well known in the art. The DNA may be used directly or may be amplified enzymatically in vitro through use of PCR (Saiki et al., Science 239:487-91, 1988) or other in vitro amplification methods such as the ligase chain reaction (LCR) (Wu et al., Genomics 4:560-69 (1989), strand displacement amplification (SDA) (Walker et al. Proc. Natl. Acad. Sci. U.S.A, 89:392-96, 1992), self-sustained sequence replication (3SR), prior to mutation analysis.

Individuals carrying polymorphic alleles may be detected by using a variety of techniques that are well known in the art. Strategies for identification and detection are described in e.g., EP 730,663, EP 717,113, and PCT US97/02102. The present methods usually employ pre-characterized polymorphisms. That is, the genotyping location and nature of polymorphic forms present at a site have already been determined. The availability of this information allows sets of probes to be designed for specific identification of the known polymorphic forms.

Detection can include amplification of the starting nucleic acid (DNA or RNA) from the target samples. This can be accomplished by e.g., PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

The detection of polymorphisms in specific DNA sequences, can be accomplished by a variety of methods including, but not limited to, restriction-fragment-length-polymorphism detection based on allele-specific restriction-endonuclease cleavage, hybridization with allele-specific oligonucleotide probes (Wallace et al., Nucl. Acids Res. 6:3543-3557, 1978), including immobilized oligonucleotides (Saiki et al., Proc. Natl. Acad. Sci. USA, 86:6230-6234, 1969) or oligonucleotide arrays (Maskos et al., Nucl. Acids Res 21:2269-2270, 1993), allele-specific PCR (Newton et al., Nucl Acids Res. 17:2503-16, 1989), mismatch-repair detection (MRD) (Faham et al., Genome Res. 5:474-482, 1995), binding of MutS protein (Wagner et al., Nucl. Acids Res. 23:3944-48, 1995), denaturing-gradient gel electrophoresis (DGGE) (Fisher et al., Proc. Natl. Acad. Sci. USA 80:1579-83, 1983), single-strand-conformation-polymorphism detection (Orita et al., Genomics 5:874-879, 1983), RNAase cleavage at mismatched base-pairs (Myers et al., Science 230: 1242, 1985), chemical (Cotton et al., Proc. Natl. Sci. U.S.A 85:4397-4401, 1988) or enzymatic (Youil et al., Proc. Natl. Acad. Sci. USA 92:87-91, 1995) cleavage of heteroduplex DNA, methods based on allele specific primer extension (Syvanen et al., Genomics 8:684-92, 1990), genetic bit analysis (GBA) (Nikiforov et al., Nucleic Acids Res. 22:4167-4175 (1994), the oligonucleotide-ligation assay (OLA) (Landegren et al., Science 241:1077, 1988), the allele-specific ligation chain reaction (LCR) (Barrany, Proc. Natl. Acad. Sci. USA 88:189-193, 1991), gap-LCR (Abravaya et al., Nucl Acids Res 23:675-682, 1995), radioactive and/or fluorescent DNA sequencing using standard procedures well known in the art, and peptide nucleic acid (PNA) assays (Orum et al., Nucl. Acids Res, 21:5332-5356, 1993; Thiede et al., Nucl. Acids Res. 24:983-984, 1996).

"Specific hybridization" or "selective hybridization" refers to the binding, or duplexing, of a nucleic acid molecule only to a second particular nucleotide sequence to which the nucleic acid is complementary, under suitably stringent conditions when that sequence is present in a complex mixture (e.g., total cellular DNA or RNA). "Stringent conditions" are conditions under which a probe will hybridize to its target subsequence, but to no other sequences. Stringent conditions are sequence-dependent and are different in different circumstances. Longer sequences hybridize specifically at higher temperatures than shorter ones. Generally, stringent conditions are selected such that the temperature is about 5° C. lower than the thermal melting point (Tm) for the specific sequence to which hybridization is intended to occur at a defined ionic strength and pH. The Tm is the temperature (under defined ionic strength, pH, and nucleic acid concentration) at which 50% of the target sequence hybridizes to the complementary probe at equilibrium. Typically, stringent conditions include a salt concentration of at least about 0.01 to about 1.0 M Na ion concentration (or other salts), at pH 7.0 to 8.3. The temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations.

The invention also provides methods for identifying polymorphisms in ACHE, PON1, and BCHE genes that are associated with anxiety levels. The association of a polymorphic form and anxiety levels is compared. A statistically significant association between a polymorphic form of the gene and anxiety levels indicates the polymorphism is associated with a particular anxiety level. The presence of this polymorphism in a subject therefore, indicates the subject has a particular anxiety level. In some embodiments, the anxiety level is determined with reference to a mean STAI score.

Assessing Anxiety by Measuring AChE Activity or Expression

The invention is based in part on the discovery that AChE activity, when corrected for demographic parameters, is inversely associated with trait anxiety. Thus, state anxiety in a subject can be assessed by comparing the amount of AChE activity in a test sample from a subject with the level of activity in a reference sample whose amount of trait anxiety is known. A lower level of AChE activity in the subject as compared to the amount of AChE activity in the reference sample indicates the subject has more trait anxiety than the individual or individuals that constitute the reference sample. Conversely, a higher level of AChE activity in the subject as compared to the amount of AChE activity in the reference sample indicates the subject has less trait anxiety than the level of trait anxiety in the individual or individuals that constitute the reference sample.

Methods of assessing AChE activity are well known (see, e.g., Ellman et al., Biochem. Pharmacol. 7:88-95, 1961). In addition to serum, the test sample can alternatively be any biological fluid, cell sample, or tissue, as long as it includes active AChE protein. Activity is measured in the presence of a BChE inhibitor, such as iso-OMPA at $5.10^{-5}$ M.

Anxiety levels can alternatively, or in addition, be assessed by examining relative levels of AChE monomeric forms relative to other AChE forms. As is discussed in detail below, AChE monomeric forms are over represented in subjects with low trait anxiety scores. Alternative splicing of AChE gene products yields at least three distinct proteins with acetylcholine hydrolytic activity. Of these, the primary AChE-S variant forms tetramers, the erythrocytic AChE-E protein appears as glycophoshoinositide-bound dimers and the stress-induced AChE-R variant remains monomeric (Soreq et al., Nat. Rev. Neurosci. 2:294-302, 2001). These forms of AChE can be resolved using methods known in the art, such as non-denaturing polyacrylamide gel electrophoresis. The resolved AChE can be visualized using various method, such as staining for activity or by immunoblot analysis.

A higher level of monomeric forms of AChE relative to the other AChE forms in the test sample indicates the subject has less trait anxiety than the individual or individuals that constitute the reference sample. A lower level of monomeric forms reveals greater trait anxiety in the subject than in the individual or individuals that constitute the reference sample.

Susceptibility to state anxiety is determined by identifying PON activity and/or AChE activity in a subject and comparing the activity to a reference sample derived from one or more individuals whose state anxiety level is known. Assays for PON activity are known in the art and are described in, e.g., Furlong et al., Anal Biochem 180:242-7, 1989. The individual or individuals in the reference sample are similar to the subject in at least one trait selected from gender, age, race, ethnic group, and body mass index. A higher level of PON in said test sample compared to said reference sample indicates the subject has increased susceptibility to state anxiety compared to said one or more individuals in said reference sample.

Further, assessing the activity of more than one enzyme may provide a more accurate measurement of susceptibility to trait anxiety relative to assessing the activity of one enzyme. As is describe in the Examples section and hereinbelow it is postulated that the functional relationship between AChE, PON and BChE activity results in the activity of all three enzymes correlating with susceptibility to trait anxiety.

Referring to FIG. 12, there are several modes of AChE and PON1 interaction at the protein level. As shown in the upper portion of FIG. 12, the first mode of AChE-PON1 interaction(s) relates to the broad antioxidative properties of PON1. PON1 protects LDL from oxidation and is an established protection factor in atherosclerosis (Mackness et al., Atheroscler Suppl, 3(4):49-55, 2002). This ability may reflect the capacity to hydrolyze lipid peroxides and hydroperoxides and to hydrolyze hydrogen peroxide (Aviram et al., J Clin Invest, 101(8):1581-90, 1998), as well as its ability to reduce oxidative stress in macrophages, including decrease in superoxide anion release (Rozenberg et al., Free Radic Biol Med, 34(6):774-84, 2003). Reciprocally, AChE is known to be particularly sensitive to oxidative stress and is inactivated under oxidative conditions (Weiner et al., Biochem Biophys Res Commun, 198(3):915-22, 1994). By reducing oxidative stress, PON1 can therefore protect plasma AChE and AChE inactivation under low PON1 levels can elevate acetylcholine levels, initiating AChE overproduction and increasing the levels of plasma AChE-R monomers.

Another mode of interaction relates to the age-dependent changes in arylesterase activity, likely mediated through the L55M position yet involving the H1, H2 helices (FIG. 12). Increased arylesterase activity may reflect changes in HDL composition, which in turn involves oxidative stress damages to AChE. This alleviates the need for AChE overproduction, suggesting that PON1 L55 carriers are better protected from cholinergic insults. That AChE-R accumulates under LPS exposure (Cohen et al., J Mol Neurosci, 21(3):199-212, 2003) may reflect the reciprocal decrease in PON1 under such exposure (Feingold et al., Atherosclerosis, 139(2):307-15, 1998.) supporting this notion. That PON1 and AChE polymorphisms were shown to predict anxiety state and trait, and that traumatic experiences can increase the anxiety level, makes carriers of debilitating PON1/ACHE polymorphisms yet more prone to adverse reactions.

Consequently, even though PON activity is inversely associated with susceptibility to state anxiety, PON activity also has an indirect inverse association with susceptibility to trait anxiety. This indirect association results from the paraoxonase, peroxidase and arylesterase activities of PON protecting AChE from oxidative stress. As a result, assessing the activity of both AChE and PON may provide a more accurate measurement of susceptibility to trait anxiety than only assessing the activity of AChE.

Similarly, through its capacity as a general scavenger of anti-AChEs, BChE has an inverse association with trait anxiety. Increasing BChE activity can protect AChE by scavenging anti-AChEs resulting in a decrease in susceptibility to trait anxiety. Consequently, assessing the activity of AChE and BChE may provide a more accurate measurement of susceptibility to trait anxiety than only assessing the activity of AChE. Further, as there is a functional relationship between all three enzymes, assessing the activity of AChE, BChE and PON may provide a more accurate measurement of susceptibility to trait anxiety than only assessing the activity of two of the enzymes.

State anxiety and/or trait anxiety can be assessed at multiple time points by measuring PON and/or AChE activity in two or more samples taken at two or more time points. Relevant time points for comparing anxiety levels include, e.g., before and after administering an anxiety treatment, as well as during and after an anxiety attack.

Treatment outcome for anxiety therapies can be assessed and predicted by measuring cholinergic enzyme activities; FIGS. 13A-13D and 14A-14D show that serum cholinergic enzyme activities correlate with anxiety scores in subjects suffering from situational (such as disease-related) anxiety, as well as primary, non-situational anxiety. Thus, it will be appreciated, that measurement of cholinergic enzyme activities can be used to determine the response of a patient to anti-anxiety treatment. Presently, such assessment of anti-anxiety treatment is typically dependent on observation of improvement in clinical anxiety symptoms and/or scores a considerable time after initiation of treatment. Thus, monitoring and adjusting the anxiety therapy to the individual needs of the patient often becomes an unduly protracted and complex process. However, in view of the correlation between cholinergic enzyme levels and anxiety, as described herein, response to anxiety treatment can be assessed biochemically, with superior accuracy and far in advance of observable clinical changes, by objective measuring cholinergic enzyme activity. Such biochemical assessment of response to treatment can allow rapid adjustment of treatment parameters such as choice of drug, dosage, regimen, etc. Assessing or monitoring response to anti-anxiety treatment, or predicting outcome of anti-anxiety treatment can be performed by measuring, in the patient, cholinergic enzyme activity, such as PON1, AChE, or monomeric AChE levels, as described herein. Measurement can be performed at single or multiple time points prior to initiation of treatment, and comparatively continued at single or multiple time points after initiation of treatment. Changes in cholinergic enzyme levels, compared to levels prior to initiation of therapy, can indicate an effect, or degree of effect of the treatment. Such monitoring can be used to adjust drug dosage, type of anti-anxiety therapy, etc. Such assessment can be performed for short- medium- or long-term monitoring of anxiety in the patient.

Such assessment of treatment outcome and efficacy by measurement of cholinergic enzymes in the patient is suitable for use with all anti-anxiety treatments. In one preferred embodiment, the anti anxiety therapy is for primary, non-situational anxiety. In another embodiment, the anti-anxiety therapy is for secondary, situational anxiety. Following is a non-limiting list of suitable therapies for anxiety: benzodiazepines such as alprazolam, clonazepam, diazepam, lorazepam, halazepam, oxazepam, and chlordiazepam; beta blockers such as propranolol, nadolol, pindolol and atenolol; tricyclic antidepressants such as imipramine, desipramine, nortriptyline, amitriptyline, doxepin, clomipramine, trazodone, and venlafaxine; monoamine oxidase inhibitors such as phenelzine, tranylcypromine, fluoxetine, fluvoxamine, sertraline, paroxetine, escitalopram oxalate and citalopram; mild tranquilizers such as buspirone; and anticonvulsants such as valproate. It will be appreciated that the progress and efficacy of non-pharmaceutical anti-anxiety therapies, such as biofeedback, psychotherapy, etc, can be assessed and monitored using measurement of cholinergic enzymes in the patient.

While reducing the present invention to practice, it was shown that depressed patients receiving anti-depression therapy showed consistent and sigificant changes in cholinergic enzyme activity (see FIGS. 14 and 15). Thus, measurement of changes in cholinergic enzymes, as described herein, can be used to monitor, assess and/or predict treatment outcomes of anti-depressant therapy. Following is a non-limiting list of anti-depression therapies suitable for use with the methods of the present invention: SSRIs such as citalopram, escitalopram oxalate, fluvoxamine, paroxetine, fluoxetine and sertraline; MAOIs such as phenelzine and tranylcypromine; Tricyclics such as doxepin, clomipramine, amitriptyline, maprotiline, desipramine, nortryptyline, trimipramine, imipramine and protriptyline; buspirone, duloxetine, trazodone, venlafaxine, reboxetine, mirtazapine, nefazodone and bupropion.

AChE/BChE and PON polymorphism can be identified using a variety of methods. One option is to determine the entire gene sequence of a PCR reaction product. Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Following is a non-limiting list of detection methods which can be used along with the present invention.

Restriction Fragment Length Polymorphism (RFLP): This method uses a change in a single nucleotide (the SNP nucleotide) which modifies a recognition site for a restriction enzyme resulting in the creation or destruction of an RFLP. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

Allele specific oligonucleotide (ASO): In this method an allele-specific oligonucleotides (ASOs) is designed to hybridize in proximity to the polymorphic nucleotide, such that a primer extension or ligation event can be used as the indicator of a match or a mis-match. Hybridization with radioactively labeled allelic specific oligonucleotides (ASO) also has been applied to the detection of specific SNPs (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles.

Denaturing/Temperature Gradient Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of SNPs in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475,1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA:RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of SNPs.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Pyrosequencing™ analysis (Pyrosequencing, Inc. Westborough, Mass., USA): This technique is based on the hybridization of a sequencing primer to a single stranded, PCR-amplified, DNA template in the presence of DNA polymerase, ATP sulfurylase, luciferase and apyrase enzymes and the adenosine 5' phosphosulfate (APS) and luciferin substrates. In the second step the first of four deoxynucleotide triphosphates (dNTP) is added to the reaction and the DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. In the last step the ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a pyrogram™. Each light signal is proportional to the number of nucleotides incorporated.

Acycloprime™ analysis (Perkin Elmer, Boston, Mass., USA): This technique is based on fluorescent polarization (FP) detection. Following PCR amplification of the sequence containing the SNP of interest, excess primer and dNTPs are removed through incubation with shrimp alkaline phosphatase (SAP) and exonuclease I. Once the enzymes are heat inactivated, the Acycloprime-FP process uses a thermostable polymerase to add one of two fluorescent terminators to a primer that ends immediately upstream of the SNP site. The terminator(s) added are identified by their increased FP and represent the allele(s) present in the original DNA sample. The Acycloprime process uses AcycloPol™, a novel mutant thermostable polymerase from the Archeon family, and a pair of AcycloTerminators™ labeled with R110 and TAMRA, representing the possible alleles for the SNP of interest. AcycloTerminator™ non-nucleotide analogs are biologically active with a variety of DNA polymerases. Similarly to 2',3'-dideoxynucleotide-5'-triphosphates, the acyclic analogs function as chain terminators. The analog is incorporated by the DNA polymerase in a base-specific manner onto the 3'-end of the DNA chain, and since there is no 3'-hydroxyl, is unable to function in further chain elongation. It has been found that AcycloPol has a higher affinity and specificity for derivatized AcycloTerminators than various Taq mutant have for derivatized 2',3'-dideoxynucleotide terminators.

Reverse dot blot: This technique uses labeled sequence specific oligonucleotide probes and unlabeled nucleic acid samples. Activated primary amine-conjugated oligonucleotides are covalently attached to carboxylated nylon membranes. After hybridization and washing, the labeled probe, or a labeled fragment of the probe, can be released using oligomer restriction, i.e., the digestion of the duplex hybrid with a restriction enzyme. Circular spots or lines are visualized colorimetrically after hybridization through the use of streptavidin horseradish peroxidase incubation followed by development using tetramethylbenzidine and hydrogen peroxide, or via chemiluminescence after incubation with avidin alkaline phosphatase conjugate and a luminous substrate susceptible to enzyme activation, such as CSPD, followed by exposure to x-ray film.

It will be appreciated that advances in the field of SNP detection have provided additional accurate, easy, and inexpensive large-scale SNP genotyping techniques, such as dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the Taq-Man system (Holland, P. M. et al., 1991. Detection of specific polymerase chain reaction product by utilizing the 5'→3' exonuclease activity, of Thermus aquaticus DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S. and Higuchi, R. Single tube genotyping without oligonucleotide probes. Genome Res. 9:72-78 (1999)], FRET primers (Solinas A et al., 2001. Nucleic Acids Res. 29: E96), AlphaScreen (Beaudet L, et al., Genome Res. 2001, 11(4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut I G. 2003. Rapid Commun. Mass. Spectrom. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab. Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu T M, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi M M. 2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) and MassArray (Leushner J, Chiu N H, 2000. Mol Diagn. 5: 341-80).

According to preferred embodiments of the present invention the SNPs used by the present invention are selected from the National Center for Biotechnology Information (http://www.ncbi.nlm.nih.gov/SNP/).

As is mentioned hereinabove and described in great detail in the Examples section which follows, the present inventors have uncovered several novel traits which can associated with ChE and PON activity:

(i) PON activity which is lower than predicted (likely due to genotype differences) reflects increased risk to develop state anxiety;

(ii) AChE activity which is lower than predicted reflects elevated trait anxiety; and (iii) PON, in its capacities as a paraoxonase or peroxidase, protects circulation AChE from oxidative stress, therefore, debilitated PON may further contribute to trait anxiety, albeit indirectly.

In addition, BChE serves to protect circulation AChE by acting as a general scavenger of anti AChEs. As such, triple assays (of AChE, BChE and PON) would be yet more reliable.

Based on these observations, the present inventor postulates that diagnosis which is effected by combined testing (of AChE, and PON and optionally BChE) and in particular, diagnosis which correlates AChE and PON activity or expression can yield more reliable predictions of anxiety parameters than single tests of either of these activities.

The usefulness and accuracy of such combined testing is clearly supported by the finding presented herein which illustrate that anxiety is a multifactorial state which depends upon discrete activities of two or more enzymes as well as the interaction therebetween.

Assessing Anxiety by Correlating ChE Activity or Expression with PON Activity or Expression As is illustrated in the Examples section which follows, the present inventors also correlated ChE/PON activity/expression levels (herein ChE/PON ratio) and uncovered that individuals predisposed to, or having anxiety display ChE/PON ratios which differ from those displayed by healthy individuals.

Thus, according to another aspect of the present invention there is provided yet another method of assessing state or trait anxiety in a subject.

Figure 6:
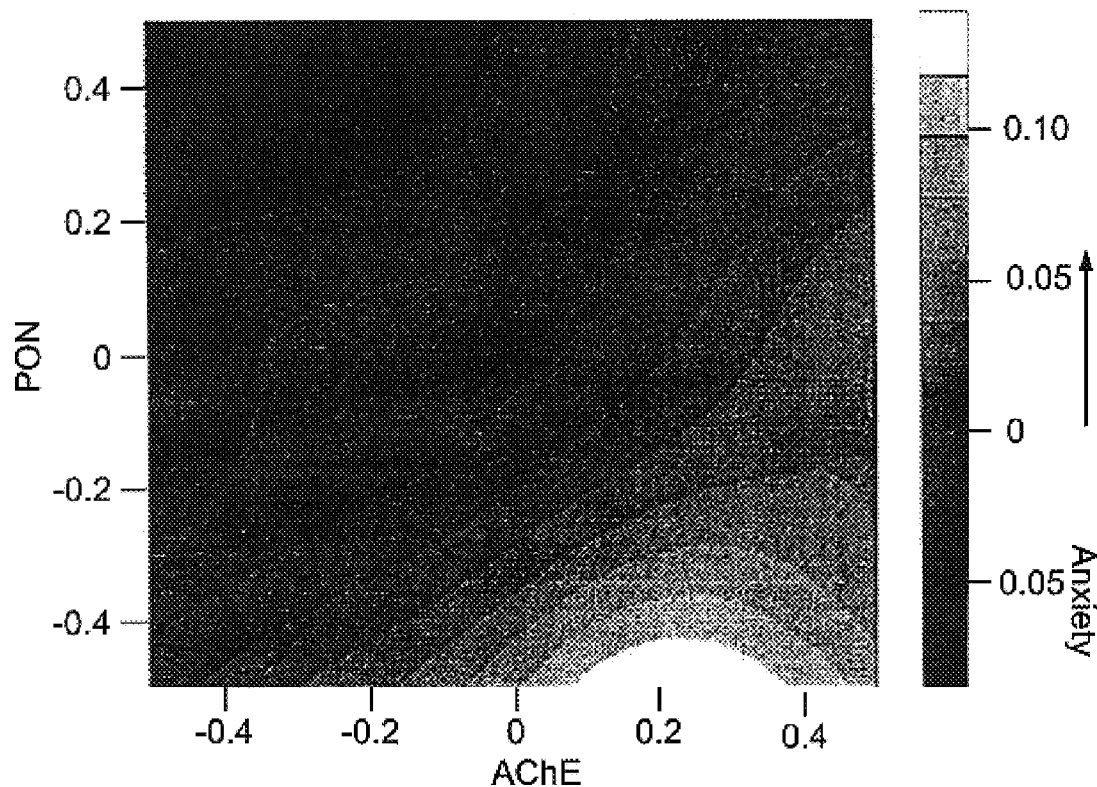

The method is effected by determining in a biological sample of an individual expression and/or activity levels of at least one cholinesterase (ChE), preferably Acetylcholinesterase (AChE) and paraoxonase (PON1); and correlating between expression and/or activity levels of the at least one cholinesterase and the paraoxonase to thereby obtain the ChE/PON ratio described herein. Such a ratio is then compared with a predetermined threshold (a single value or preferably a value range) predefined for healthy or diseased individuals of a specific group (age, gender BMI, ethnicity, race etc.), to thereby diagnose the subject as healthy, having anxiety or being predisposed thereto. Further description of this ratio is provided in the examples section which follows, and illustrated in FIG. 6.

It will be appreciated that quantification of ChE (preferably AChE) and PON expression or activity levels can be facilitated using one of several known approaches.

The above described expression and/or activity levels can be determined by allele typing and correlation of a specific allele with expression/activity levels. Since a correlation between allele types and expression levels can be established, mere typing of an allele can be translated into expression or activity levels of ChE or PON.

Biochemical or molecular analysis of test samples can also be used to determine the above described ratio. Numerous approaches for measuring mRNA or protein levels in a biological sample such as blood are known in the art, most of these approaches are readily adaptable for high throughput automatic screening. Examples of suitable approaches are provided below.

Northern Blot analysis: This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, calorimetric reaction or chemiluminescence. This method allows both quantitation of an amount of particular RNA molecules and determination of its identity by a relative position on the membrane which is indicative of a migration distance in the gel during electrophoresis.

RT-PCR analysis: This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA in situ hybridization stain: In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a calorimetric reaction which reveals signals generated using enzyme-linked labeled probes.

In situ RT-PCR stain: This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Although cell profiling methods which analyze the genome or transcriptome are preferred for their accuracy and high throughput capabilities, it will be appreciated that the present invention can also utilize protein analysis tools for profiling the cells of the cultures.

Expression and/or activity level of proteins can be determined using any of the methods described below.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a calorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In situ activity assay: According to this method, a chromogenic substrate is applied on the cells containing an active enzyme and the enzyme catalyzes a reaction in which the substrate is decomposed to produce a chromogenic product visible by a light or a fluorescent microscope.

In vitro activity assays: In these methods the activity of a particular enzyme is measured in a protein mixture extracted from the cells. The activity can be measured in a spectrophotometer well using calorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

It will be appreciated that anxiety diagnosis obtained via the ChE/PON ratio determination described above, offers several advantages over discrete AChE or PON expression/activity. One notable advantage is a lack of need for control samples. Since a ratio does not rely upon absolute numbers but rather on the relationship therebetween, ratio-determined diagnosis does not necessitate comparison with control samples nor does it necessitate standardization of results with respect to age or gender but rather generation of a single threshold for each tested group. For example, groups of similar ethnic background, age, gender or BMI can be used to generate a threshold ratio which can be used to determine diagnosis of individuals belonging to a specific group.

It will be appreciated that any of the reagents described hereinabove (e.g., AChE or PON PCR primers or probes) can be packaged into a kit which can be used for state or trait anxiety diagnosis, or monitoring treatment or therapy outcomes of situational and non-situational anxiety, or monitoring treatment or therapy outcomes of anti-depressants. The kit for use in the method according to the invention preferably contains the various components needed for carrying out the method packaged in separate containers and/or vials and including instructions for carrying out the method. Thus, for example, some or all of the various reagents and other ingredients needed for carrying out the determination, such as buffers, primers, enzymes, control samples or standards etc can be packaged separately but provided for use in the same box. Instructions for carrying out the method can be included inside the box, as a separate insert, or as a label on the box and/or on the separate vials.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Polymorphisms in the ACHE1-PON1 and BCHE Genes are Predictors of Trait Anxiety

The psychological phenomenon of anxiety that is experienced by individuals at a certain time (state anxiety) differs from their general susceptibility to anxiety (trait anxiety). To investigate the role of cholinergic regulation in both of these measures, DNA, sera, and data on the state anxiety and trait anxiety measures from 451 individuals from the HERITAGE Family Study (Bouchard et al., *Medicine and Science in Sports and Exercise* 27:721-29, 1995).

As part of the study questionnaire measures of state and trait anxiety were obtained on a subset of the families. A total of 461 individuals (198 men, 263 women) from 150 two-generation families of African-American (172), or Caucasian origin (289) with complete data were compared.

Genomic DNA was prepared from permanent lymphoblastoid cells using proteinase K and phenol/chloroform extraction. DNA was dialyzed four times against 10 mM Tris 1 mM EDTA (pH 8.0) buffer (6 h, at 4° C.), and ethanol-precipitated. Genotyping involved PCR amplification of the corresponding gene regions, using Taq polymerase (Sigma, St. Louis, Mo.) followed by agarose gel electrophoresis and Exo-Sap enzymatic purification (USB, Cleveland, Ohio) of the PCR product. Standard automated sequencing utilized the BigDye Terminator cycle sequencing chemistry, ABI 3700 DNA Analyzer and Data collection and Sequence Analysis software (Applied Biosystems, Foster City, Calif.). The reactions employed are detailed under Table 3.

The 55L/M and 192Q/R polymorphisms in PON1 were detected using the single nucleotide primer extension method (SNaPshot ddNTP Primer Extension kit, ABI). Following PCR amplification and purification the SNaPshot reaction was performed using the PON1 probes 5'-GGCA-GAAACTGG CTCTGAAGAC-3' (SEQ ID NO: 13) for 55L/M and 5'-GATCACTAT TTTCTTGACCCCTACTTAC-3' (SEQ ID NO: 14) for 192Q/R. Following extension and calf intestine phosphatase treatment (Amersham Biosciences, Freiburg, Germany), the products were electrophoresed on a 3700 ABI analyzer and the results analyzed with Genescan software.

The studied population included 150 two-generation families. To reduce the effect of non-observed variables that influence the parameter of interest a family membership indicator was included. P values for the difference between the genotypes of the subjects with a trait anxiety score in the upper and lower 20% or 50% groups were calculated using the Likelihood Ratio Test. The P value was the exact conditional tail probability given the marginal as was assessed by 100,000 Monte Carlo simulations. P values for the differences between AChE, BChE and PON activities were calculated using 2-tailed Student's t-test. Multiple regression analysis was done using R, statistical software (Ihaka et al., Journal Computational and Graphical Statistics 5:299-314, 1996).

Classification trees were grown using the R library tree (Breiman et al., Classification and Regression Trees, Wardsworth (London, UK) 1984; Ripley, Pattern Recognition and Neural Networks, Chapter 7, Cambridge University Press, 1996), which attempts to build a model explaining the relation between a response and a predictor that cannot be well approximated by a linear model. The tree is built from a sequence of questions that can be answered by yes or no and a set of fitted response values. Depending on the answer to a question, the tree leads to a second question or to a fitted response value. The tree function in the R software was used to define a sequence of binary partitions of the population into subsets based on age, gender and the different enzyme activities. Classification trees were "grown" such that at each step the resulting subsets were the most homogeneous with respect to the membership in the top 20% state anxiety group. The tree was then "pruned" to a number of subsets, or "nodes", which is determined by minimizing the misclassification error by a 20-fold cross-validation. The process is automatic after selection of the relevant variables for the analysis.

Figure 1:
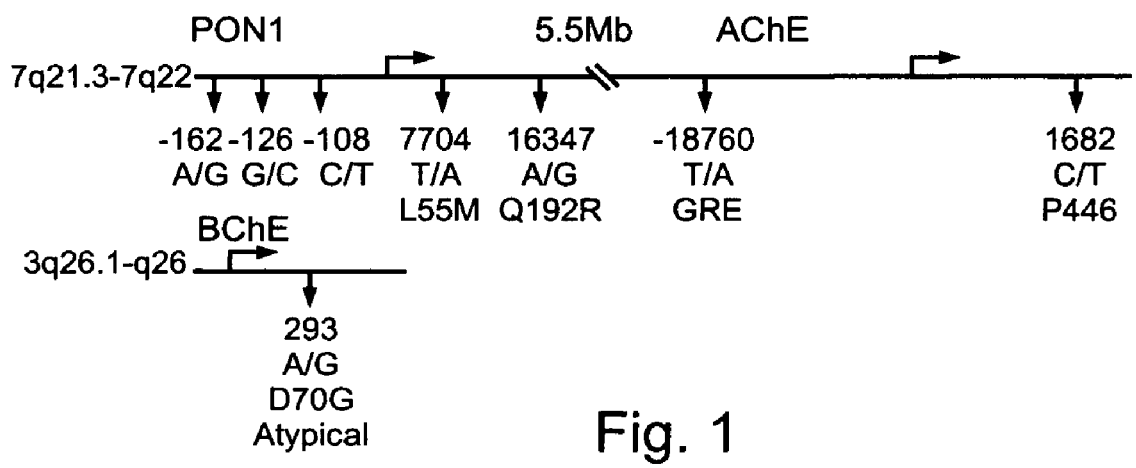

Mean STAI scores were 35±12 (range 20-80) for trait anxiety and 35±9 (range 16-73) for state anxiety. These values are within the range reported by others, albeit for far smaller groups with disease-associated anxiety symptoms (Nakamura et al., Pyschopharmacology 162:301-03, 2002; Seki et al., Circ. J. 67:73-77, 2003; Wolf et al., J. Clin. Pyschopharmacol. 23:51-57, 2003). Potential genomic correlates for this tendency were sought in the ACHE locus. The extended human ACHE promoter includes a functional glucocorticoid response element (GRE), suggesting a responsiveness of expression to stress. Israeli subjects frequently carry at this region a deletion that causes constitutive over-expression of blood AChE associated with acute anti-AChE hypersensitivity (Shapira et al., Hum. Mol. Genet. 9:1273-81, 2000). However, it was found that this deletion is exceedingly infrequent in the U.S. population (0.34% vs. 3.64% allele frequency in Israelis). Therefore, a second ACHE linkage marker, ACHE's biochemically ineffective P446 polymorphism, was used instead. This marker occurred at an 11.3% frequency in the HERITAGE subjects (Bartels et al., Am. J. Hum. Genet. 52-928-36, 1993; FIG. 1).

The research was extended to two more genes and enzymes contributing to balanced ACh regulation: the AChE-related ACh hydrolyzing enzyme butyrylcholinesterase, BChE, (and the BCHE gene) and the organophosphate hydrolyzing enzyme Paraoxonase, PON (and the PON1 gene), involved in the protection of cholinergic neurotransmission from environmental challenges (Li et al., Toxicol. Lett. 76:219-26, 1995). Three known PON1 promoter polymorphisms (indicated by the distance in nucleotides from the transcription start site at 0) were examined: −108 C/T which contributes to 22.4% of the variation in PON1 expression, possibly by eliminating a potential SP1 transcription factor binding site (Suehiro et al., Atherosclerosis 150:295-98, 2000); −162 G/C which contributes to only 2.4% of this variation (Brophy et al., Am. J. Hum. Genet. 68:1428-36, 2001) and −126 C/G which has no apparent effect on PON1 expression level (Costa et al., Ann. Ref. Med. 54:371-92, 2003).

In the PON1 coding region, the following substitutions were genotyped (indicated by amino acid number and symbol) of L55M (CTG into ATG), reducing PON protein and mRNA levels (Garin et al., J. Clin. Invest. 99:62-66, 1997) and Q192R (CAA into CGA), which affects PON's catalytic efficiency (Davies et al., Nat. Genet. 14:334-36, 1996). The following BCHE mutations were genotyped: the D70G substitution yielding the "atypical" BChE variant with enzymatic activity 30% lower than the wild type enzyme (Neville et al., J. Biol. Chem. 265:20735-38, 1990). Homozygous carriers of this polymorphism display extreme anxiety following exposure to anti-AChEs (e.g. Loewenstein-Lichtenstein et al., Nat. Med. 1:1082-85, 1995). The frequency of this allele in the HERITAGE Family Study was 2.3%, considerably lower than the frequency of 6% found in Israelis (Ehrlich et al., Genomics 22:288-95, 1994). The PON1 and ACHE genes are both located on the long arm of chromosome 7, with 5.5 mega bases (Mb) separating between them, whereas the BCHE gene is located on the long arm of chromosome 3. Therefore, joint effects of PON1 and ACHE but not BCHE polymorphisms, could reflect cis effects. FIG. 1 displays the polymorphic sites that were studied in the ACHE, BCHE and PON1 genes.

Significantly different genotype frequencies were found in the analyzed sites between subjects with a trait but not state anxiety score in the highest and lowest decile. Members of the high trait anxiety group included significantly more subjects heterozygous for the P446 polymorphism in ACHE ($p<7.2\times 10^{-9}$) and significantly more subjects homozygous for the PON192 polymorphism ($p<4\times 10^{-7}$). Members of the lower trait anxiety group included significantly more subjects heterozygous for the PON-108 and 162 polymorphisms ($p<9\times 10^{-7}$, $p<0.001$ respectively, $Xi^2$ test, Table 1).

TABLE 1

Genotype frequencies in groups with the highest and lowest trait anxiety deciles as compared with the total population.

|  | Genotype | top decile | n | bottom decile | P value |
| --- | --- | --- | --- | --- | --- |
| AChE P446 | C/C | 31 (66%) | 289 (82%) | 44 (85%) | 0.02* |
| (1431 C/T) | C/T | 16 (34%) | 51 (15%) | 7 (13%) |  |
|  | T/T | 0 | 12 (3%) | 1 (2%) |  |
| PON-108 C/T | C/C | 21 (46%) | 134 (39%) | 13 (25.5%) | 0.06 |
|  | C/T | 12 (27%) | 125 (37%) | 25 (49%) |  |
|  | T/T | 12 (27%) | 82 (24%) | 13 (25.5%) |  |
| PON-126 G/C | G/G | 43 (96%) | 319 (93%) | 47 (92%) | 1 |
|  | G/C | 2 (4%) | 20 (6%) | 4 (8%) |  |
|  | C/C | 0 | 2 (1%) | 0 |  |
| PON-162 G/A | G/G | 9 (20%) | 40 (12%) | 5 (10%) | 0.3 |
|  | G/A | 12 (27%) | 114 (33%) | 19 (38%) |  |
|  | A/A | 24 (53%) | 187 (55%) | 26 (52%) |  |
| PON 55 L/M | L/L | 20 (43%) | 162 (46%) | 24 (46%) | 0.86 |
| (162 T/A) | L/M | 21 (46%) | 155 (44%) | 21 (40%) |  |
|  | M/M | 5 (11%) | 32 (9%) | 7 (14%) |  |
| PON 192 Q/R | Q/Q | 14 (31%) | 120 (35%) | 24 (46%) | 0.08 |
| (575 A/G) | Q/R | 19 (41%) | 146 (42%) | 22 (42%) |  |
|  | R/R | 13 (28%) | 82 (23%) | 6 (12%) |  |
| "Atypical" BChE | A/A | 44 (100%) | 333 (95%) | 51 (98%) | 1 |
| 70D/G (293 A/G) | A/G | 0 | 16 (5%) | 1 (2%) |  |
| AChE GRE-17133 T/A | T/T | 43 (100%) | 331 (99%) | 48 (98%) | 1 |
|  | T/A | 0 | 2 (1%) | 1 (2%) |  |

*Statistical significance ($Xi^2$ test). A total of 451 subjects was tested.

Because of the population admixture of Afro-Americans and Caucasians, the possibility of false positives due to population stratification combined with trait and allele differences was tested. Both Afro-American and Caucasian subjects presented significant differences between the top and bottom trait anxiety deciles in the PON1 gene; Afro-Americans also differed in the ACHE gene ($p<2\times10^{-6}$) and Caucasians in the BChE gene ($p<2.6\times10^{-6}$). Thus, although both the anxiety mean trait and the genotype and allele frequencies differed significantly between populations (Afro-Americans 36.1±9.5, Caucasians 33.7±8.4, T-test, $p<0.006$ for trait anxiety and $p<0.00002$, $p<5\times10^{-9}$, $p<0.001$, $p<0.00001$ for P446, PON108, PON162 and PON192 respectively) significant and relevant anxiety-associated differences were found in both populations for the tested genes.

Another control test involved the analysis of a single sibling from each family, chosen randomly as independent individuals from both the Afro-American and the Caucasian groups (a total of 163 individuals). To enlarge the sample size after these divisions these groups were divided evenly into subjects with high or low trait anxiety scores. In this case as well, the PON gene displayed significant differences for both Afro-Americans and Caucasians ($p<0.01$, $0.02$, respectively). Caucasians also showed significant differences in the BChE gene ($p<0.0002$) but the ACHE polymorphism appeared less significant ($p<0.07$) and only in Afro-Americans. Based on these findings, the analysis was performed of the entire population as a single group.

Joint consideration of polymorphism pairs revealed yet more significant contributions of P446 with PON108 ($p<0.006$), or with PON192 ($p<0.001$), as well as for PON108 with PON126 ($p<0.007$) or PON126 with PON162 ($p<0.006$) to the trait anxiety score (Table 2). Polymorphisms in the ACHE-PON1 and BCHE loci thus appeared to be significant, albeit ethnic origin dependent predictors of trait anxiety, either due to the modified phenotype they caused or because of linkage disequilibrium to other polymorphisms.

TABLE 2

Joint PON1 and AChE contributions to trait anxiety scores*.

| | | Trait anxiety | | | | | P |
|---|---|---|---|---|---|---|---|
| | top 50% | | | lower 50% | | | value |

1. AChE P446 (1431 C/T)

PON-108 C/T

| | CT | TT | CC | | CT | TT | CC | |
|---|---|---|---|---|---|---|---|---|
| CT | 10 | 6 | 18 | CT | 9 | 0 | 20 | 0.006* |
| TT | 0 | 0 | 7 | TT | 0 | 1 | 4 | |
| CC | 61 | 43 | 62 | CC | 70 | 53 | 32 | |

PON-126 G/C

| | GC | CC | GG | | GC | CC | GG | |
|---|---|---|---|---|---|---|---|---|
| CT | 1 | 0 | 33 | CT | 1 | 0 | 28 | 0.2 |
| TT | 0 | 0 | 7 | TT | 1 | 0 | 4 | |
| CC | 5 | 1 | 160 | CC | 17 | 1 | 137 | |

PON-162 G/A

| | GA | AA | GG | | GA | AA | GG | |
|---|---|---|---|---|---|---|---|---|
| CT | 8 | 21 | 3 | CT | 13 | 10 | 6 | 0.03 |
| TT | 3 | 3 | 1 | TT | 3 | 2 | 0 | |
| CC | 67 | 80 | 19 | CC | 38 | 102 | 15 | |

TABLE 2-continued

Joint PON1 and AChE contributions to trait anxiety scores*.

| | | Trait anxiety | | | | | P |
|---|---|---|---|---|---|---|---|
| | top 50% | | | lower 50% | | | value |

PON 55 L/M (162 T/A)

| | TA | AA | TT | | TA | AA | TT | |
|---|---|---|---|---|---|---|---|---|
| CT | 17 | 3 | 14 | CT | 6 | 1 | 22 | 0.2 |
| TT | 2 | 0 | 5 | TT | 3 | 0 | 2 | |
| CC | 73 | 20 | 73 | CC | 74 | 15 | 66 | |

PON 192 Q/R (575 A/G)

| | AG | GG | AA | | AG | GG | AA | |
|---|---|---|---|---|---|---|---|---|
| CT | 10 | 9 | 15 | CT | 14 | 12 | 3 | 0.001* |
| TT | 0 | 6 | 1 | TT | 3 | 0 | 2 | |
| CC | 66 | 37 | 63 | CC | 74 | 24 | 57 | |

"Atypical" BChE 70D/G (293 A/G)

| | AG | AA | | AG | AA | |
|---|---|---|---|---|---|---|
| CT | 1 | 33 | CT | 2 | 27 | 0.1 |
| TT | 0 | 7 | TT | 0 | 5 | |
| CC | 5 | 161 | CC | 6 | 149 | |

AChE GRE-17133 T/A

| | TA | TT | | TA | TT | |
|---|---|---|---|---|---|---|
| CT | 2 | 32 | CT | 0 | 26 | 0.5 |
| TT | 0 | 7 | TT | 0 | 5 | |
| CC | 1 | 157 | CC | 0 | 147 | |

2. PON-103 C/T

PON-126 G/C

| | GC | CC | GG | | GC | CC | GG | |
|---|---|---|---|---|---|---|---|---|
| CT | 5 | 0 | 66 | CT | 9 | 0 | 70 | 0.007* |
| TT | 0 | 0 | 49 | TT | 1 | 0 | 53 | |
| CC | 1 | 1 | 85 | CC | 9 | 1 | 46 | |

PON-162 G/A

| | GA | AA | GG | | GA | AA | GG | |
|---|---|---|---|---|---|---|---|---|
| CT | 39 | 30 | 2 | CT | 29 | 50 | 0 | 0.01 |
| TT | 0 | 49 | 0 | TT | 0 | 53 | 1 | |
| CC | 49 | 25 | 23 | CC | 25 | 11 | 20 | |

PON 55 L/M (162 T/A)

| | TA | AA | TT | | TA | AA | TT | |
|---|---|---|---|---|---|---|---|---|
| CT | 35 | 10 | 26 | CT | 40 | 4 | 35 | 0.09 |
| TT | 28 | 10 | 11 | TT | 28 | 8 | 18 | |
| CC | 29 | 3 | 55 | CC | 15 | 4 | 37 | |

PON 192 Q/R (575 A/G)

| | AG | GG | AA | | AG | GG | AA | |
|---|---|---|---|---|---|---|---|---|
| CT | 28 | 10 | 33 | CT | 38 | 14 | 27 | 0.02 |
| TT | 25 | 3 | 21 | TT | 26 | 7 | 21 | |
| CC | 23 | 39 | 25 | CC | 27 | 15 | 14 | |

"Atypical" BChE 70D/G (293 A/G)

| | AG | AA | | AG | AA | |
|---|---|---|---|---|---|---|
| CT | 3 | 68 | CT | 3 | 76 | 0.2 |
| TT | 2 | 47 | TT | 4 | 50 | |
| CC | 1 | 86 | CC | 1 | 55 | |

TABLE 2-continued

Joint PON1 and AChE contributions to trait anxiety scores*.

AChE GRE-17133 T/A

| | Trait anxiety top 50% | | | Trait anxiety lower 50% | | P value |
|---|---|---|---|---|---|---|
| | TA | TT | | TA | TT | |
| CT | 1 | 69 | CT | 0 | 73 | 0.05 |
| TT | 2 | 43 | TT | 0 | 52 | |
| CC | 0 | 84 | CC | 0 | 53 | |

3. PON-126 G/C

PON-162 G/A

| | GA | AA | GG | | GA | AA | GG | P value |
|---|---|---|---|---|---|---|---|---|
| GC | 5 | 1 | 0 | GC | 13 | 1 | 5 | 0.006* |
| CC | 0 | 0 | 1 | CC | 0 | 0 | 1 | |
| GG | 73 | 103 | 24 | GG | 41 | 113 | 15 | |

PON 55 L/M (162 T/A)

| | TA | AA | TT | | TA | AA | TT | P value |
|---|---|---|---|---|---|---|---|---|
| GC | 4 | 0 | 2 | GC | 4 | 3 | 12 | 0.05 |
| CC | 0 | 0 | 1 | CC | 0 | 0 | 1 | |
| GG | 83 | 23 | 89 | GG | 79 | 13 | 77 | |

PON 192 Q/R (575 A/G)

| | AG | GG | AA | | AG | GG | AA | P value |
|---|---|---|---|---|---|---|---|---|
| GC | 3 | 2 | 1 | GC | 10 | 5 | 4 | 0.03 |
| CC | 0 | 1 | 0 | CC | 0 | 0 | 1 | |
| GG | 73 | 49 | 73 | GG | 81 | 31 | 57 | |

"Atypical" BChE 70D/G (293 A/G)

| | AG | AA | | AG | AA | P value |
|---|---|---|---|---|---|---|
| GC | 0 | 6 | GC | 0 | 19 | 0.08 |
| CC | 0 | 1 | CC | 0 | 1 | |
| GG | 6 | 194 | GG | 8 | 161 | |

AChE GRE-17133 T/A

| | TA | TT | | TA | TT | P value |
|---|---|---|---|---|---|---|
| GC | 0 | 6 | GC | 0 | 18 | 0.4 |
| CC | 0 | 1 | CC | 0 | 1 | |
| GG | 3 | 189 | GG | 0 | 150 | |

4. PON-162 G/A

PON 55 L/M (162 T/A)

| | TA | AA | TT | | TA | AA | TT | P value |
|---|---|---|---|---|---|---|---|---|
| GA | 34 | 1 | 43 | GA | 17 | 5 | 32 | 0.02 |
| AA | 52 | 21 | 31 | AA | 61 | 9 | 44 | |
| GG | 6 | 1 | 18 | GG | 5 | 2 | 14 | |

PON 192 Q/R (575 A/G)

| | AG | GG | AA | | AG | GG | AA | P value |
|---|---|---|---|---|---|---|---|---|
| GA | 36 | 20 | 22 | GA | 30 | 10 | 14 | 0.02 |
| AA | 38 | 17 | 49 | AA | 53 | 21 | 40 | |
| GG | 2 | 15 | 8 | GG | 8 | 5 | 8 | |

"Atypical" BChE 70D/G (293 A/G)

| | AG | AA | | AG | AA | P value |
|---|---|---|---|---|---|---|
| GA | 3 | 75 | GA | 1 | 53 | 0.3 |
| AA | 3 | 101 | AA | 7 | 107 | |
| GG | 0 | 25 | GG | 0 | 21 | |

AChE GRE-17133 T/A

| | TA | TT | | TA | TT | P value |
|---|---|---|---|---|---|---|
| GA | 1 | 76 | GA | 0 | 51 | 0.07 |
| AA | 2 | 95 | AA | 0 | 109 | |
| GG | 0 | 25 | GG | 0 | 18 | |

5. PON 55 L/M (162 T/A)

PON 192 Q/R (575 A/G)

| | AG | GG | AA | | AG | GG | AA | P value |
|---|---|---|---|---|---|---|---|---|
| TA | 44 | 6 | 42 | TA | 40 | 3 | 40 | 0.09 |
| AA | 4 | 1 | 13 | AA | 2 | 1 | 13 | |
| TT | 28 | 43 | 19 | TT | 49 | 32 | 9 | |

"Atypical" BChE 70D/G (293 A/G)

| | AG | AA | | AG | AA | P value |
|---|---|---|---|---|---|---|
| TA | 1 | 91 | TA | 4 | 79 | 0.6 |
| AA | 1 | 22 | AA | 1 | 15 | |
| TT | 4 | 83 | TT | 3 | 87 | |

AChE GRE-17133 T/A

| | TA | TT | | TA | TT | P value |
|---|---|---|---|---|---|---|
| TA | 3 | 86 | TA | 0 | 77 | 0.5 |
| AA | 0 | 21 | AA | 0 | 15 | |
| TT | 0 | 89 | TT | 0 | 86 | |

6. PON 192 Q/R (575 A/G)

"Atypical" BChE 70D/G (293 A/G)

| | AG | AA | | AG | AA | P value |
|---|---|---|---|---|---|---|
| AG | 2 | 76 | AG | 4 | 87 | 0.1 |
| GG | 2 | 50 | GG | 0 | 36 | |
| AA | 2 | 77 | AA | 4 | 58 | |

AChE GRE-17133 T/A

| | TA | TT | | TA | TT | P value |
|---|---|---|---|---|---|---|
| AG | 8 | 73 | AG | 0 | 86 | 0.1 |
| GG | 8 | 31 | GG | 0 | 34 | |
| AA | 3 | 72 | AA | 0 | 58 | |

7. "Atypical" BChE 70D/G (293 A/G)

AChE GRE-17133 T/A

| | TA | TT | | TA | TT | | |
|---|---|---|---|---|---|---|---|
| AG | 0 | 8 | AG | 0 | 7 | AG | |
| AA | 3 | 190 | AA | 0 | 171 | AA | |

*comparison of the top 50% and the lower 50% of the joint most significant distributions of two genetic locations.

TABLE 3

PCR conditions for genotyping the different polymorphisms

| Gene (Accession No.) | Polymorphism | Primers | Product Size | PCR Conditions |
|---|---|---|---|---|
| ACHE (AF002993) | GRE T/A | (+) 5'GTGAGAATGGCTG CTTCATA-3' (SEQ ID NO: 1)<br>(−) 5'CTCAGTTCTGGGAAATTCCTA-3' (SEQ ID NO: 2) | 217 bp | 60° C., 37 cycles |
|  | P446 C/T | (+) 5'-CGGGTCTACGCCTACGTCTTTGAACACC GTGCTTC-3' (SEQ ID NO. 3)<br>(−) 5'-CCCGTCCTTTCTGTCTCGTGTG-3' (SEQ ID NO: 4) | 328 bp | 55° C., 37 cycles 5% DMSO |
| BCHE (AC009811) | Atypical (D70G) A/G | (+) 5'CTTGGTAGACTTCGATTCAAAAAGCCACAGTCT-3' (SEQ ID NO: 5)<br>(−) 5'GAATCCATACATTTAGATATAAACA GTCTTCACTG-3' (SEQ ID NO: 6) | 187 BP | |
| PON1 (AF539592) | PON-108 C/T PON-126 G/C PON-162 G/A | (+) 5'ACTGAATCT CTC TGAGACGCAAGGACC3' (SEQ ID NO: 7)<br>(−) 5'ATAGACAAAGGGATCGATGGGCGCA GACA3' (SEQ ID NO: 8) | 376 bp | 60° C., 37 cycles, 5% DMSO |
|  | PON55 L/M T/A | (+) 5'-GAAGAGTGATGTATAGCCCCAG-3' (SEQ ID NO: 9)<br>(−) 5'-ACACTCACAGAGCTAATGAAAGCC-3' (SEQ ID NO: 10) | 178 bp | |
|  | PON192 Q/R A/G | (+) 5'GGAATAGACAGTGAGGAATGCCAGT3' (SEQ ID NO: 11)<br>(−) 5'CAGAGAGTTCACATACTTGCCATCGG3' (SEQ ID NO: 12) | 305 bp | |

Example 2

The Selective Association of Specific ACHE Genotypes with Anxiety is Reflected in Serum AChE Activities The selective association of specific ACHE and PON1 genotypes with the anxiety scores of individual subjects is reflected in their serum AChE, BChE and PON activities as affected by inherited and/or acquired influences.

Blood samples were collected at baseline in the morning after a 12-hour fast. Serum was prepared by centrifugation of the blood at 2,000 g (15 min, 4° C.). Aliquots of 2 mL in cryogenic tubes were frozen at 80° C. until use. Questionnaires were completed later that morning. Serum PON activity was determined by an adaptation of the spectrophotometric method (Furlong et al., Anal. Biochem. 180:242-47, 1989) to a microtiter plate assay. Ten μL of diluted (1:10) serum were incubated in duplicates with 190 μL of 1.2 mM diethyl p-nitrophenyl phosphate (Paraoxon, Sigma,) in 0.26 mM Tris-HCl, pH 8.5, 25 mM $CaCl_2$ and 0.5 M NaCl. Readings at 405 nm were repeated at 2-min intervals for 10 min. Non-enzymatic hydrolysis of paraoxon was subtracted. Enzyme activity was calculated using the molar extinction coefficient for p-nitrophenol [17,100 $M^{-1} \cdot cm^{-1}$] (Furlong et al., Anal. Biochem. 180:242-47, 1989).

Serum cholinesterase catalytic activity measurements were based on a spectrophotometric method adopted to a microtiter plate assay. Acetylthiocholine (ATCh, Sigma,) or butyrylthiocholine (BTCh, Sigma,) hydrolysis rates were measured following 20 min incubation with $5 \cdot 10^{-5}$ M tetraisopropyl pyrophosphoramide (iso-OMPA, Sigma,), a specific BChE inhibitor or $10^{-5}$ M 1,5-bis(4-allyldimethylammoniumphenyl) pentan-3-one dibromide (BW284c51, Sigma, A9013), a specific AChE inhibitor. Addition of both inhibitors reduced hydrolysis to the rate of spontaneous hydrolysis measured in control reactions lacking enzyme or substrate, attesting to the specificity of these serum activities. Readings at 405 nm were repeated at 2-min intervals for 20 min. Non-enzymatic hydrolysis of substrate was subtracted from the total rate of hydrolysis. Enzyme activity was calculated using the molar extinction coefficient for 5-thio-2-nitrobenzoate [13,600 $M^{-1} \cdot cm^{-1}$] (Ellman et al., Biochem Pharmacol. 7:88-95, 1961).

Cortisol levels were assayed using a radioimmunoassay kit (Diagnostic Systems Laboratories Inc., Webster, Tex.) as described (Feitosa et al., Metabolism 51:360-65, 2002).

Figure 2:
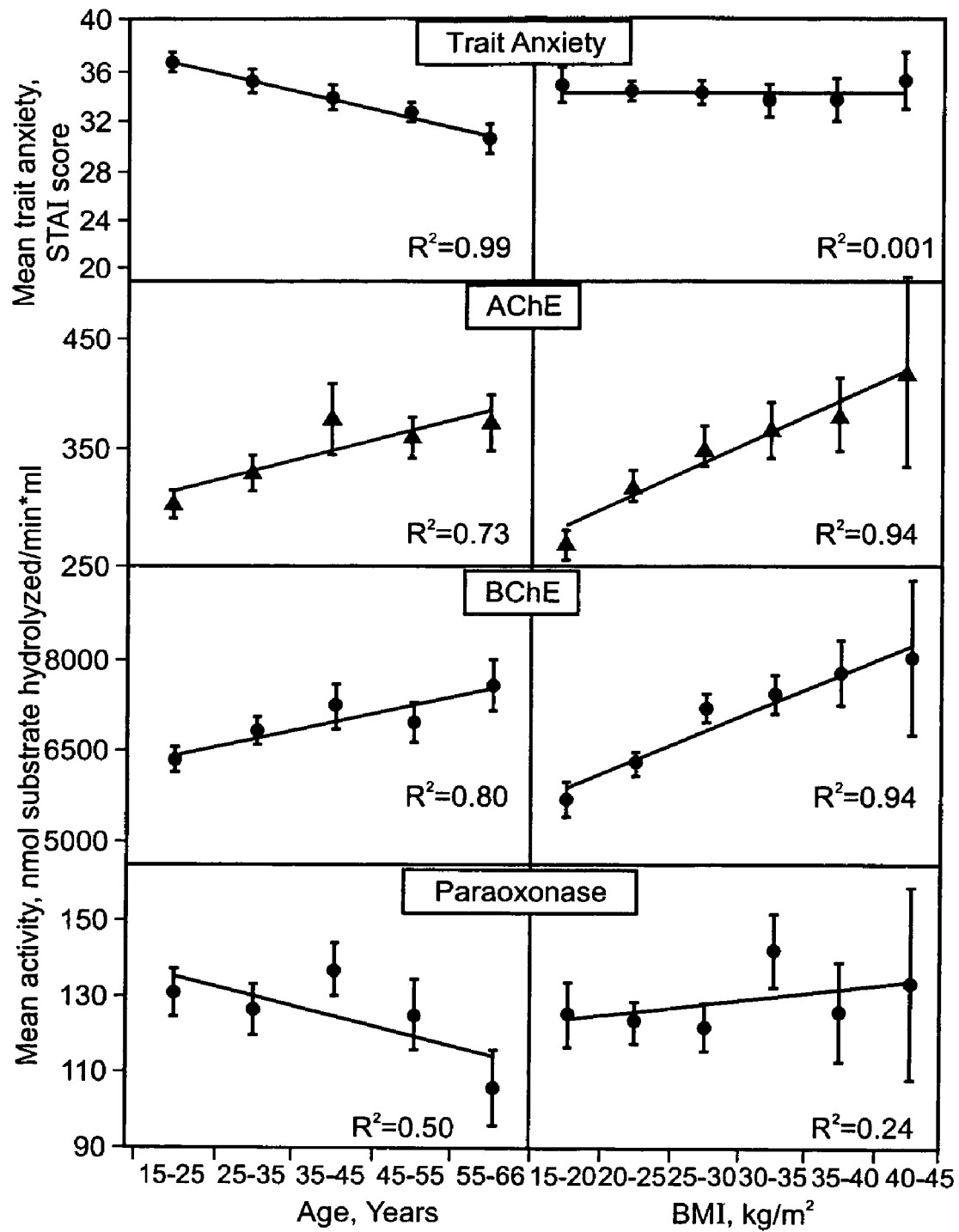
Figure 3:
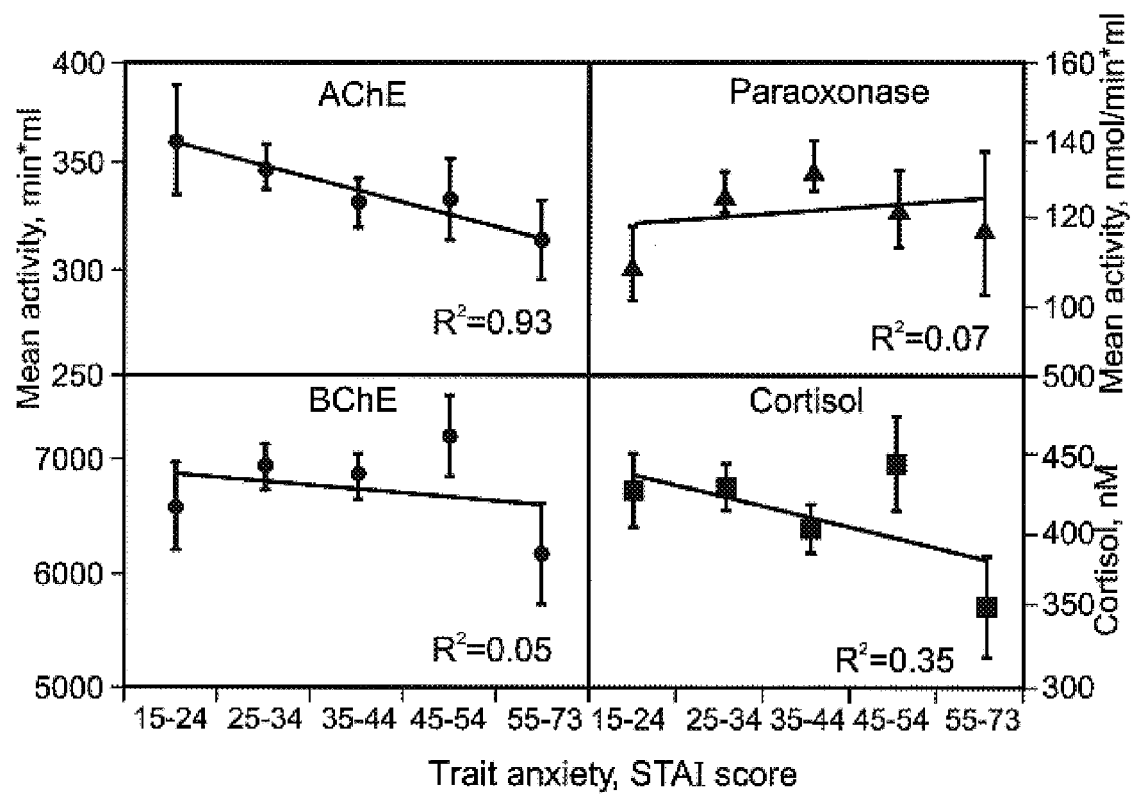

Trait, but not state anxiety scores showed decreases with age (FIG. 2 and data not shown), suggesting that one's experience and/or age provide better protection from trait, but not state anxiety. Significantly higher activities in AChE and BChE but not in PON activities were found with in females as opposed to males (2-tailed Student's t-test, $p<0.006$ and $p<0.0002$ as compared to $p>0.2$, respectively). Also, significantly higher AChE serum activity was found in individuals of Caucasian origins ($p<0.002$). In contrast, PON was significantly higher in African-Americans ($p<3\times10^{-10}$). BChE activity showed no significant differences between the above populations ($p>0.5$). AChE and BChE levels increased with age and body mass index (BMI), whereas PON activity declined with age. FIG. 2 presents these acquired changes in serum enzyme activities. Compatible with these age-associated changes, an inverse correlation was found between AChE, but not BChE or PON activities and trait but not state anxiety (FIG. 3). Intriguingly, PON but not BChE or AChE activity displayed an inverse association with state anxiety ($R^2=0.89$). That serum AChE activity increased in parallel to the age-related reduction in trait anxiety suggested a trait anxiety predictive role for this enzyme's activities in the serum. Cortisol levels, however, did not correlate with trait anxiety scores, in agreement with the apparent equivocal relationship between emotional distress and cortisol (Vedhara et al., Biol. Psychol. 62:89-96, 2003).

Potential inter-relationships between the different enzyme activities were indicated by the AChE/BChE correlations, which were highly significant in subjects of both ethnic origins ($R^2=0.73$, 0.56 for Afro-Americans and Caucasians, respectively). However, AChE/PON showed no straightforward interactions.

To further characterize the anxiety-associated serum AChE in subjects of Caucasian origin, non-denaturing gel electrophoresis followed by activity staining was performed, and the relative amounts of tetrameric, dimeric, and monomeric forms of AChE were examined.

Figure 4:
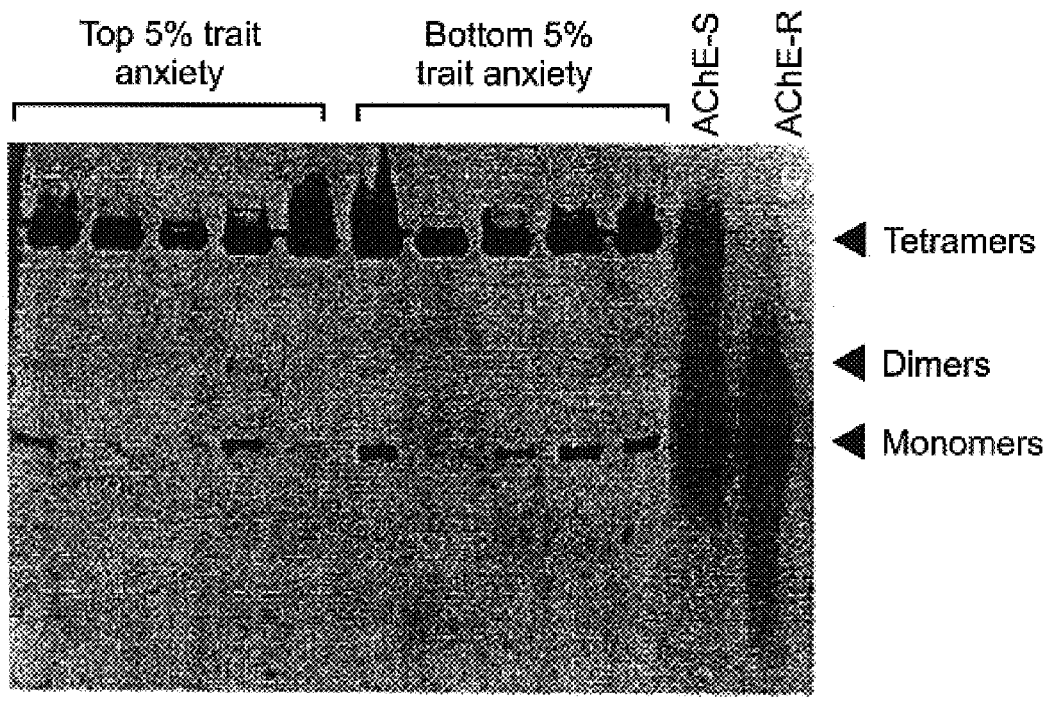

All serum samples displayed active tetramers with very small amounts of dimers; however, active monomers appeared to be over-represented in serum samples from Caucasian subjects with lowest trait anxiety scores as compared to those with highest scores. FIG. 4 presents several examples for these differences. Immuno-labeling of serum protein blots suggested that serum AChE monomers represent AChE-R (see also Brenner et al., FASEB J. 17:214-22, 2003). Therefore, this analysis supported the notion that the capacity of the tested Caucasian subjects to respond to external stimuli by over-producing monomeric AChE-R is associated with their reduced trait anxiety scores.

Correlations between serum biochemical markers and trait anxiety were next calculated for all subjects after normalizing the effect of age, ethnic origin, gender and BMI. Testing individuals who presented the top 20% trait anxiety scores against the rest of the population using a generalized linear model (with a logistic link function) showed a significant effect of both the genotyped polymorphisms ($p<0.013$) and the serum activity levels of AChE, BChE and PON ($p<0.022$) on the trait anxiety score. In a regression analysis testing for factors contributing to the trait anxiety scores, there was a clear effect of all the polymorphisms genotyped together with gender, age and ethnic origin on PON serum activities ($p<5.4\times10^{-7}$). A smaller, but significant effect was observed on AChE ($p<0.03$) and BChE activities ($p<0.04$). Thus, the inherited parameters which contribute significantly to the measured enzyme activities further predict a considerable fraction of the quantified trait anxiety scores with significant power.

The measured effects were largely independent of family links. Out of the whole data set, 92 families with at least 2 siblings were identified. Two siblings in each family were randomly chosen for further analysis. Next, the difference between the serum variables of the two siblings and the difference between their anxiety variables were calculated. Within families, sibling correlations were low both for anxiety variables (i.e. trait and state anxiety) and for serum activities (AChE, BChE and PON), indicating a major contribution of environmental and experience-derived factors.

The subset of the population whose trait anxiety scores distributed in the top 20% of analyzed subjects were then identified using the classification and regression tree method (Breiman et al., Classification and Regression Trees, Wardsworth (London, UK) 1984).

Figure 5:
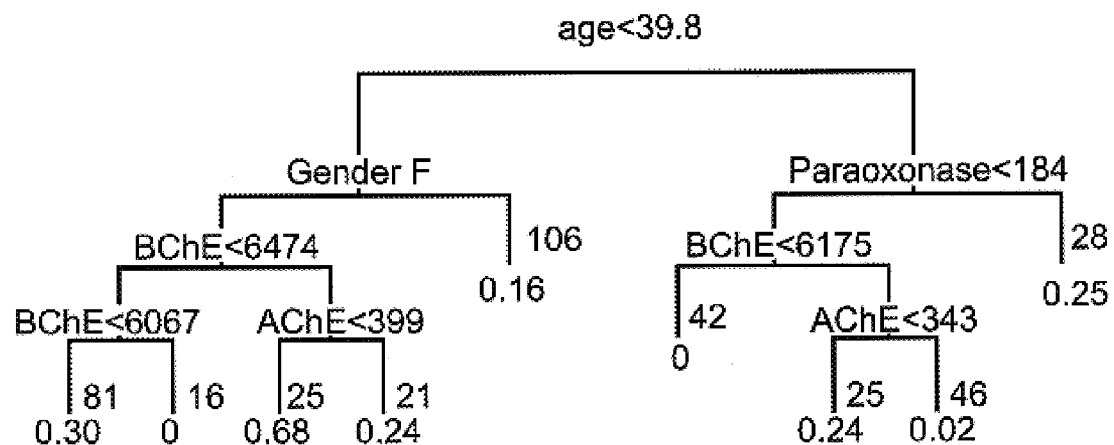

This tree growing process is performed automatically after choosing the relevant variables by an algorithm in the R program. The "pruned" tree, presented in FIG. 5, supported protective power of serum AChE activity from the trait anxiety phenotype as well as its interaction with other enzyme activities. Thus, for example subjects 40 years old and above with lower than 184 nmol hydrolyzed substrate/min*ml PON activity but AChE and BChE activities higher than 6175 and 343 nmol /min*ml, respectively, would have only 2% chance of belonging to the 20% top trait anxiety group, regardless of their gender.

Finally, the difference between trait and state anxiety was assessed. For example, subjects with increased serum AChE activity and elevated serum AChE monomers were found unlikely to display high trait anxiety scores. Therefore, the ACHE gene in these subjects was close to its maximal expression capacity. This implied limited ability of such subjects to react to a changing environment by overproducing AChE. In view of the stress-suppressing role of overproduced AChE (Kaufer et al., Nature 393:373-77, 1998) this further predicted elevated susceptibility for state anxiety in individuals with higher than expected serum AChE activities, unless another condition(s) is met which compensates for this property. To test this working hypothesis, the difference of one's state anxiety from the expected average value of all the tested subjects was calculated and plotted as a function of the parallel differences from their predicted serum AChE and PON activities corrected for age, gender, BMI and ethnic origin. This yielded a significant two-dimensional interaction (at $p<0.004$, using ANOVA), plotted in FIG. 6. The resultant interaction implied that subjects with exceptionally low PON activities may be at greater susceptibility to develop state anxiety under conditions that fail to trigger the activation of the AChE feedback response. This susceptibility would be larger for Caucasian subjects due to their lower PON activities (FIG. 2), explaining their associated AChE and trait anxiety. In conclusion, serum AChE activities and their interaction with PON activities displayed distinct predictive associations with trait and state anxiety scores.

These findings correlate significantly with the psychologically examined anxiety scores of the HERITAGE Family Study subjects. In addition, such correlations were common for individuals of diverse ethnic origins. This supports the notion that these biochemical and ethnic origin-dependent genetic factors are causally related to anxiety: either they cause or mediate anxiety, or, when enzyme activities are involved, anxiety causes them. These results add cholinergic regulation and the ACHE/PON1 locus to the findings of others of genetic components to anxiety (Hariri et al., Science 297:400-03, 2002). Attributing to the difference between observed and expected AChE activity a causal role in state anxiety is further compatible with the present findings that the suppression of the stress-induced AChE-R variant obliterates conflict behavior (Cohen et al., Molecular Psychiatry 7:874-85, 2002; Birikh et al., Proc. Natl. Acad. Sci. USA 100:283, 2003). That anxiety is affected by polymorphisms in the PON1 and BCHE genes, both having an AChE protective function emphasizes the stress placed on AChE by environmental challenges.

The contribution of PON1 polymorphisms toward serum enzyme activities and as risk factors for various diseases has been extensively discussed (Costa et al., Ann. Rev. Med. 54:271-92, 2003). Intriguingly, the L55M polymorphism in PON1, which was reported to increase the risk for cardiovascular disease in diabetes (Garin et al., J. Clin. Invest. 99:62-66, 1997) was found only marginally effective and only in conjunction with the P446 ACHE polymorphism for anxiety scores. As the P446 polymorphism in ACHE is biochemically ineffective (Bartels et al., Am. J. Hum. Genet. 52:928-36, 1993), its calculated prediction power of anxiety scores may reflect the contribution of adjacent sequences in the ACHE-PON1 locus to the expression of these and/or other genes whose functions may be relevant to the control over anxiety feelings. This could be, for example, a phenotypically effective mutation in another closely positioned gene, e.g., ARS2 (Grant et al., Cell. Mol. Neurobiology. 21:783-97, 2001).

The apparent relationship between AChE and PON activities may have several origins. First, these genes are closely positioned on the long arm of chromosome 7 and may be co-regulated, so that a polymorphism in one of them may affect the other by a cis mechanism (Balciuniene et al., Hum Genet. 110:1-7, 2002). Second, both AChE and PON are targets of organophosphates: PON hydrolyzes them and AChE is inhibited, by them (Furlong et al., Neurotoxicology 21:581-87, 2000). Therefore, subjects with high PON activity may less frequently need the AChE feedback response, which is, essential under exposure (e.g. to insecticide remaining in fresh crops, (see McGehee et al., Anesthesiology 93:510-19, 2000)) for those with low PON levels. Third, PON has been reported to confer protection from oxidative stress (Durrington et al., Arteriolscler. Thromb. Vasc. Biol. 21:473-80, 2001), to which AChE was shown to be particularly sensitive (Weiner et al., Biochem. Biophys. Res. Comm. 198:915-22, 1994). Each of these pathways alone, or a combination of them, can lead to the observed inter-relationships between the two enzymes.

The observed contribution of ACh regulation to the anxiety scores of otherwise healthy subjects may further be relevant to the recently reported role of ACh in controlling the production of pro-inflammatory cytokines (Bernik et al., J. Exp. Med. 195:781-88, 2002). Thus, the anxiety-associated role of such cytokines (Anisman et al., Ann. Med. 35:2-11, 2003) likely contributes to their reported effects in a plethora of autoimmune, atherosclerosis and aging-related diseases. Increased serum AChE, and consequently decreased ACh, would alleviate the attenuation over release by macrophages of pro-inflammatory cytokines. Therefore, one's serum AChE levels may serve as an inverse predictor of ACh's power to suppress inflammatory responses. This may explain the known higher risk for inflammatory diseases with increasing age and BMI (Saito et al., Circ. J. 67:323-39, 2003). Anxiety scores, in generally healthy subjects, may hence be relevant both for psychological and physiological symptoms. That they may be evaluated by genomic and biochemical measures reflecting the cholinergic balance in the circulation provides a previously unforeseen approach for studying and perhaps controlling human anxiety.

Example 3

Application of Regression Analysis for Predicting Serum Enzyme Activities in Healthy Individuals AChE: To predict the expected serum AChE activity, in nmol substrate hydrolyzed per ml per min, in healthy individuals, the available demographic data are incorporated into the following equation and multiplied by the residual coefficients calculated by regression analysis for the Heritage cohort.

Race: 0=African American
    1=Caucasian
Sex: 0=male
    1=female

Residual Coefficients for Serum AChE Activity

A. AChE: Expected AChE activity=sex (as-0- or -1-)×−25.8840+age×1.1311+race (as -0- or -1-)×55.5682+BMI×6.3681 $[P<3.3\times10^{-9}]$

| Parameter | Coefficient | Standard Error | t Value | Significance$^{(P)}$ |
|---|---|---|---|---|
| Sex | −25.8840 | 14.84881 | −1.7431 | 0.08201 |
| Age | 1.1311 | 0.56021 | 2.0191 | 0.04409* |
| Race | −55.56821 | 16.03041 | 3.4661 | 0.00058*** |
| BMI | 6.36811 | 1.40201 | 4.542 | 7.22e−06*** |

B. PON: Expected PON activity=sex×0.5491+race×(−41.7841)+age×(−0.3208)+BMI×0.2201 $[P<3.80\times10^{-8}]$

| Parameter | Coefficient | Standard Error | t Value | Significance$^{(P)}$ |
|---|---|---|---|---|
| Sex | 0.5491 | 6.7381 | 0.081 | 0.935 |
| Age | −0.3208 | 0.2542 | −1.262 | 0.208 |
| Race | −41.7841 | 7.2700 | −5.747 | 1.71e−08*** |
| BMI | 0.2201 | 0.6357 | 0.346 | 0.729 |

C. BChE: Expected BChE activity=sex×(−793.487)+race×267.908+age×13.461+BMI×112.441 $[P<1.12\times10^{-9}]$

| Parameter | Coefficient | Standard Error | t Value | Significance$^{(P)}$ |
|---|---|---|---|---|
| Sex | −793.487 | 238.696 | −3.324 | 0.000962*** |
| Age | 13.461 | 9.005 | 1.495 | 0.135706 |
| Race | 267.908 | 257.691 | 1.040 | 0.299080 |
| BMI | 112.441 | 22.537 | 4.989 | 8.79e−07*** |

Example 4

Application of Regression Analysis for Predicting State and Trait Anxiety Values To predict state and trait anxiety values for tested individuals, the demographic and biochemical data are incorporated into the following equation and multiplied by the residual coefficients calculated by regression analysis for the Heritage cohort.

D. State anxiety=sex (as-0- or -1-)×1.9290+age×(−0.027)+race (as-0- or -1-)×5.7220+serum AChE activity (in nmol substrate hydrolyzed per ml per min)×(0.014)+serum BChE activity×9.52×10$^{·14}$+serum PON activity×(−0.0148)+cortisol concentration (in nM)×6.25×10$^{−4}$ [P<0.05]

E. Trait anxiety=sex×0.2956+age+×(−0.1170)+race×(−3.4610)+AChE activity×(−0.0129)+BChE activity×0.0006+PON activity×0.0083+cortisol concentration×0.0039 [P<0.06]

Residual Coefficients for Anxiety Regression Analyses

| I. State Anxiety | | | | |
|---|---|---|---|---|
| Parameter | Coefficient | Standard Error | t Value | Significance$^{(P)}$ |
| Sex | +1.9290 | 1.3050 | 1.478 | 0.1406 |
| Age | −0.0269 | 0.0470 | −0.573 | 0.5671 |
| Race | +5.7220 | 2.7660 | 2.068 | 0.0396* |
| Ache | −0.0139 | 0.0090 | −1.620 | 0.1065 |
| Bche | +0.0009 | 0.0005 | 1.977 | 0.0490* |
| PON | −0.0148 | 0.0112 | −1.322 | 0.1873 |
| Cort | −0.0006 | 0.0035 | −0.181 | 0.8564 |

| II. Trait Anxiety | | | | |
|---|---|---|---|---|
| Parameter | Coefficient | Standard Error | t Value | Significance$^{(P)}$ |
| Sex | +0.2956 | 1.0390 | 0.285 | 0.7762 |
| Age | −0.1170 | 0.0374 | −3.128 | 0.0020* |
| Race | −3.4610 | 2.2020 | 1.572 | 0.1171 |
| Ache | −0.0129 | 0.0068 | −1.889 | 0.0600* |
| Bche | +0.0006 | 0.0004 | 1.611 | 0.1083 |
| PON | +0.0082 | 0.0089 | 0.925 | 0.3557 |
| Cort | −0.0039 | 0.0027 | −1.406 | 0.1609 |

Example 5

ACHE/PON1 Allele Frequencies in the Israeli Population

Polymorphisms in the ACHE/PON1 locus were genotyped, and linkage disequilibrium was calculated for some of the polymorphisms. Additionally, the allele frequencies of PON1 and ACHE polymorphisms were calculated.

A total of 157 generally healthy individuals, (91 males, 34.2±8.9 years of age from reserve units of the Israeli Defense Forces and 66 males and females from the Herzog Hospital geriatric center, 80.1±8.2 years of age) were available for this study. Both Ashkenazi and Sephardic Jews were included. Only Herzog Hospital elder samples were genotyped. Blood samples were drawn to BD Vacutainer® blood collection tubes (Becton-DickinsonFranklin Lakes, N.J., USA ) with citrate as an anticoagulant, and centrifuged (1300 rcf, 4° C., 15 min) in an Eppendorf centrifuge to obtain plasma. Whole blood and plasma were maintained at −70° C. until use. Subjects filled a questionnaire assessing general health status, medicine intake and demographic parameters. The study was approved by the Helsinki committees for human studies of the Israeli Army Medical Corps and the Hebrew University of Jerusalem.

Genomic DNA was prepared from blood cells using the Gentra Whole Blood DNA Extraction Kit (Gentra, Minneapolis, Minn.). Genotyping involved PCR amplification of the corresponding gene regions, using Taq polymerase (Sigma, Israel) followed by agarose gel electrophoresis and Exo-Sap enzymatic purification (USB, Cleveland, Ohio) of the PCR product. Standard automated sequencing utilized the BigDye Terminator cycle sequencing chemistry, ABI 3700 DNA Analyzer and Data collection and Sequence Analysis software (Applied Biosystems, Foster City, Calif.). The reactions are detailed under Table 4. PON1 192Q/R and PON1 55L/M polymorphisms were detected using the single nucleotide primer extension method (SNaPshot ddNTP Primer Extension kit, Applied Biosystems).

Following PCR amplification and purification the SNaPshot reaction was performed using probe 5′-GGCA-GAAACTGG CTCTGAAGAC-3′ (SEQ ID NO: 13) for the PON1 55 and 5′-GATCACTAT TTTCTTGACCCCTACT-TAC -3′ (SEQ ID NO: 14) for PON1 192. Following extension and calf intestine phosphatase treatment (Amersham Biosciences, Freiburg Germany), products were electrophoresed on a 3700 ABI analyzer and the results analyzed with Genescan software (ABI).

Four promoter (ACHE −17130 TGTT deletion, PON1 −162 A/G, PON1 −126 G/C and PON1 −108 C/T) and three coding region polymorphisms (ACHE 964 C/A H322N, PON1 7704 T/A L55M and PON1 16347 A/G Q192R) in the ACHE/PON1 locus were genotyped in 157 Israelis at the age range 20-93. Together these spanned a distance of 5.5 Mb on Chr. 7q21.3-22 and covered inherited variations in both the expression potency and hydrolytic efficiency of these two genes (FIG. 1). None of the examined alleles deviated from the Hardy-Weinberg equilibrium, compatible with findings in US populations (Sklan, E. H., et al., Proc Natl Acad Sci USA, 101(15):5512-7, 2004). Linkage disequilibria D′ and $r^2$ correlation values were calculated for the PON1 55, PON1 192 and ACHE ΔHNF3β polymorphisms (Table 5).

TABLE 5

Linkage disequilibria D′ and $r^2$ correlation values for certain polymorphisms

|  | ΔHNF3β | 55 | 192 |
|---|---|---|---|
| p-values of D′ | | | |
| ΔHNF3β | 1 | 0.34 | 0.03 |
| 55 | $9.7 * 10^{-18}$ | 1 | $9.7 * 10^{-18}$ |
| 192 | 0.03 | 0.34 | 1 |
| $r^2$ | | | |
| ΔHNF3β | 1 | 0.007 | 0.026 |
| 55 | 0.007 | 1 | 0.27 |
| 192 | 0.026 | 0.27 | 1 |

TABLE 4

PCR conditions for genotyping the different polymorphisms

| Gene (Accession No.) | Polymorphism | Primers | Product Size | PCR Conditions |
|---|---|---|---|---|
| ACHE (AF002993) | ΔHNF3β T/A | (+) 5′GTGAGAATGGCTG CTTCATA3′ (SEQ ID NO: 1) <br> (−) 5′CTCAGTTCTGGGAAATTCCTA3′ (SEQ ID NO: 2) | 217 bp | 60° C., 37 cycles |
|  | H322N C/A | (+) 5′-GTAGATGGAGACTTCCTCAGTG-3′ (SEQ ID NO: 15) <br> (−) 5′-AGAGATGAACAGTTACAGACCC-3′ (SEQ ID NO: 16) | 328 bp | 55° C., 37 cycles 5% DMSO |
| PON1 (AF539592) | PON-108 C/T <br> PON-126 G/C <br> PON-162 G/A | (+) 5′ACTGAATCT CTC TGAGACGCAAGGACC3′ (SEQ ID NO: 7) <br> (−) 5′ATAGACAAAGGGATCGATGGGCGCAGACA3′ (SEQ ID NO: 8) | 376 bp | 60° C., 37 cycles, 5% DMSO |
|  | PON55 L/M T/A | (+) 5′-GAAGAGTGATGTATAGCCCCAG-3′ (SEQ ID NO: 9) <br> (−) 5′-ACACTCACAGAGCTAATGAAAGCC-3′ (SEQ ID NO: 10) | 178 bp | |
|  | PON192 Q/R A/G | (+) 5′GGAATAGACAGTGAGGAATGCCAGT3′ (SEQ ID NO: 11) <br> (−) 5′CAGAGAGTTCACATACTTGCCATCGG3′ (SEQ ID NO: 12) | 305 bp | |

The two coding region polymorphisms in PON1 presented substantial linkage disequilibrium ($r^2>0.25$), corresponding to previous reports in the US population (Brophy, V. H., et al., linkage of the 55L allele with 192R was found. In this sample, this linkage was complete: 192R and 55M never appeared together (Table 6).

TABLE 6

Allele frequencies of the PON1 and ACHE polymorphisms in different populations

| Position, allele | Israel[a] | Caucasian/USA[b] | | African/USA[c] | | Europe[d] | | Japan[e] | |
|---|---|---|---|---|---|---|---|---|---|
| PON1 | | | | | | | | | |
| -162 | | | | | | | | | |
| A | 0.18 | 0.23 | (0.070) | 0.59 | **(9.7 * 10$^{-26}$)** | ND | | 0.10 | (0.004) |
| G | 0.82 | 0.77 | | 0.41 | | ND | | 0.90 | |
| -126 | | | | | | | | | |
| G | 0.97 | ND | | 0.97 | 1 | ND | | 0.91 | (0.001) |
| C | 0.03 | ND | | 0.03 | | ND | | 0.09 | |
| -108 | | | | | | | | | |
| C | 0.40 | 0.50 | **(3.5 * 10$^{-3}$)** | 0.83 | **(2.3 * 10$^{-27}$)** | 0.46 | (0.078) | 0.48 | (0.045) |
| T | 0.60 | 0.50 | | 0.17 | | 0.54 | | 0.52 | |
| 162 (55) | | | | | | | | | |
| T (L) | 0.61 | 0.64 | (0.354) | 0.83 | **(1.2 * 10$^{-9}$)** | 0.65 | (0.215) | 0.94 | **(1.6 * 10$^{-23}$)** |
| A (M) | 0.39 | 0.36 | | 0.17 | | 0.35 | | 0.06 | |
| 575 (192) | | | | | | | | | |
| A (Q) | 0.67 | 0.73 | (0.048) | 0.34 | **(2.6 * 10$^{-16}$)** | 0.69 | (0.522) | 0.40 | **(8.9 * 10$^{-12}$)** |
| G (R) | 0.33 | 0.27 | | 0.66 | | 0.31 | | 0.60 | |
| ACHE | | | | | | | | | |
| -17130 | | | | | | | | | |
| ΔHNF3β | 0.019 | 0.003[f] | **(4.9 * 10$^{-4}$)** | <0.003 | | ND | | ND | |
| 964 H322N | 0.084 | 0.05[g] | (0.267) | ND | | ND | | ND | |
| N | 157 | 376 | | 152 | | 374 | | 161 | |

Note
low frequency of the PON1-108C allele and high frequency of the ACHE ΔHNF3β mutation in Israelis. Chi-test p-values (parentheses) are in comparison to Israel.
**Bold - p < 5 * 10$^{-3}$**.
ND—not determined.
[a]this study
[b]Brophy et al., 2001
[c]Sklan et al., 2004
[d]Leviev & James, 2000
[e]Suehiro et al., 2000
[f]Shapira et al, 2000 (n = 816)
[g]Bartels et al, 1993 (n = 38)

Am J Hum Genet 68(6):1428-36, 2001). In the ACHE gene the promoter deletion ΔHNF3β displayed a significant D' value for PON1 192 but not for PON1 55, with low $r^2$ values for both PON1 polymorphisms. This reflects the different frequencies for the ΔHNF3β and PON1 alleles in the Israeli population.

Allele frequencies in the Israeli population emerged as being closer to those reported for Caucasians, and different from Japanese and African (Table 6). However, even when compared to the tested Caucasian population in USA, the Israeli population appeared distinct, with small but significant differences in both PON1 -108 and PON1 Q192R. Particularly, the tested population included larger fractions of the lower-efficiency promoter alleles in both PON1 (-108T) and ACHE (-17130 deletion). Also, the ΔHNF3β promoter deletion and the H322N coding region substitution in ACHE were both more abundant in Israelis as compared with US subjects. Within the PON1 coding region, 6 out of 9 possible genotypes at positions 55 and 192 were found, with 15, 19, 23, 11, 18 and 14% frequencies for the MMQQ, MLQQ, MLQR, LLQQ, LLQR and LLRR genotypes, respectively. Most abundant were MLRQ heterozygotes for both polymorphisms (23% of the tested population). In agreement with previous reports, Example 6

Inherited and Acquired Variabilities in Plasma Enzyme Activities

The amount of variability in plasma enzyme activity differs for paraoxonase, arylesterase and cholinesterase. Similarly, AChE, BChE and arylesterase showed an age-dependent increase in enzyme activity, whereas PON1 did not show such a correlation.

Plasma paraoxonase activity was determined by an adaptation of the spectrophotometric method to a microtiter plate assay (Furlonget al., Anal Biochem, 180(2):242-7, 1989).

Since several variations of the assay were published, the assay was calibrated for plasma dilution and substrate concentration. A 1:5 dilution of plasma and 1.2 mM paraoxon concentration was optimal, yielding high variability as reported for paraoxonase activity. Higher substrate concentrations (up to 6 mM) enabled higher hydrolysis rates but yielded lower variability, thus obscuring the population trends. Briefly, 10 μl of plasma diluted 1:5 were placed in microtiter plate wells (Nunc, Roskilde, Denmark) in triplicate; reaction was initiated by adding 190 μl of the substrate, 1.2 mM paraoxon (Sigma), in 0.26 mM Tris-HCl, pH 8.5, 25 mM $CaCl_2$ and 0.5 M NaCl. Readings at 405 nm were repeated at minimal intervals for 10 min. Non-enzymatic breakdown of paraoxon was subtracted from the total rate of hydrolysis.

Enzyme activity was calculated using the $\epsilon_{405}$ for p-nitrophenol, 17,100 $M^{-1}cm^{-1}$. Plasma arylesterase activity was measured in 10 μl of 1:40 diluted plasma mixed with 190 μl of substrate (3.26 mM phenylacetate in 9 mM Tris-HCl pH 8 and 0.9 mM $CaCl_2$). Hydrolysis rates were determined at minimal intervals in UV-transparent 96-well plates (Greiner-Bio One GmbH, Frickenhausen, Germany), at 270 nm for 4 min. Enzyme activity was calculated using the $\epsilon_{270}$ for phenol, 1310 $M^{-1}cm^{-1}$.

Plasma cholinesterase catalytic activity measurements involved adaptation of a spectrophotometric method to a microtiter plate assay (Ellman et al., Biochem. Pharmacol., 7:88-95, 1961).

Acetylthiocholine (ATCh, Sigma, 1 mM) or butyrylthiocholine (BTCh, Sigma, 10 mM) hydrolysis rates were measured following 20 min pre-incubation with $5 \cdot 10^{-5}$ M tetraisopropyl pyrophosphoramide (iso-OMPA, Sigma), a specific BChE inhibitor, or $10^{-5}$ M 1,5-bis(4-allyldimethylammoniumphenyl)pentan-3-one dibromide (BW284C51, Sigma), a specific AChE inhibitor. Readings at 405 nm were repeated at 2-min intervals for 20 min. Non-enzymatic breakdown of substrate was subtracted from the total rate of hydrolysis. Enzyme activities were calculated using the $\epsilon_{405}$ for 5-thio-2-nitrobenzoate, 13,600 $M^{-1}cm^{-1}$.

Figure 7A:
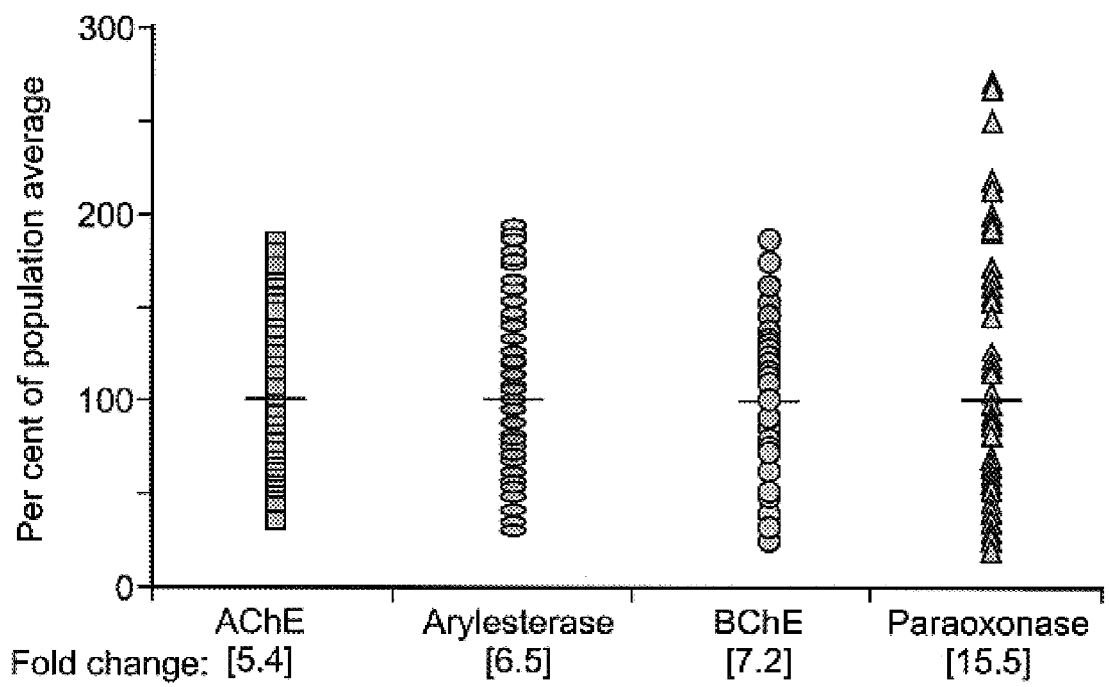

Plasma measurements highlighted pronounced variability in paraoxonase activity, the highest plasma PON1 activity being over 15-fold greater than the lowest (FIG. 7A). In contrast, the arylesterase activity of PON1 (measured as the rate of phenyl acetate hydrolysis) demonstrated moderate variability (up to 6.5-fold), reflecting specific promoter and coding region polymorphisms (Brophy et al., Am J Hum Genet, 68(6):1428-36, 2001). BChE, which serves as a natural OP scavenger, showed 7.2-fold variability, explained by many genetic variations (Ehrlich et al., Genomics, 22(2):288-95, 1994). AChE activity in plasma constitutes a small but measurable fraction of cholinesterase activity (Brenner et al., Faseb J, 17(2):214-22, 2003; Sorensen et al., Clin Chim Acta, 158(1):1-6, 1986; Zakut et al., Cancer, 61(4):727-37, 1988). Moderate variability in plasma AChE activity (over 5-fold difference between the highest and lowest values) likely reflects a combined effect of the few reported polymorphisms with expression variabilities of the ACHE gene (Shapira et al., Hum Mol Genet, 9(9):1273-81, 2000 and Sklan et al., Proc Natl Acad Sci USA, 101(15):5512-7, 2004).

Two reported genetic variations in the coding region of ACHE, a "silent" mutation in position P446 and a substitution in position 322 (H322N), (Bartels et al., Am J Hum Genet, 52(5):928-36, 1993) leading to the rare YTb blood group, do not influence AChE activity (Soreq & Seidman, Neurosci, 2(4):294-302, 2001). The promoter deletion at the HNF3β transcription factor binding site, associated with constitutive over-expression in transfected cells contributes to the observed variability in carriers (4% of tested individuals) (Shapira et al., Hum Mol Genet, 9(9):1273-81, 2000). Feedback overexpression of AChE under stress, anxiety or exposure to anti-AChEs also provides a significant contribution toward such variability (Meshorer et al., Science, 295(5554):508-12, 2002).

Figure 7B:
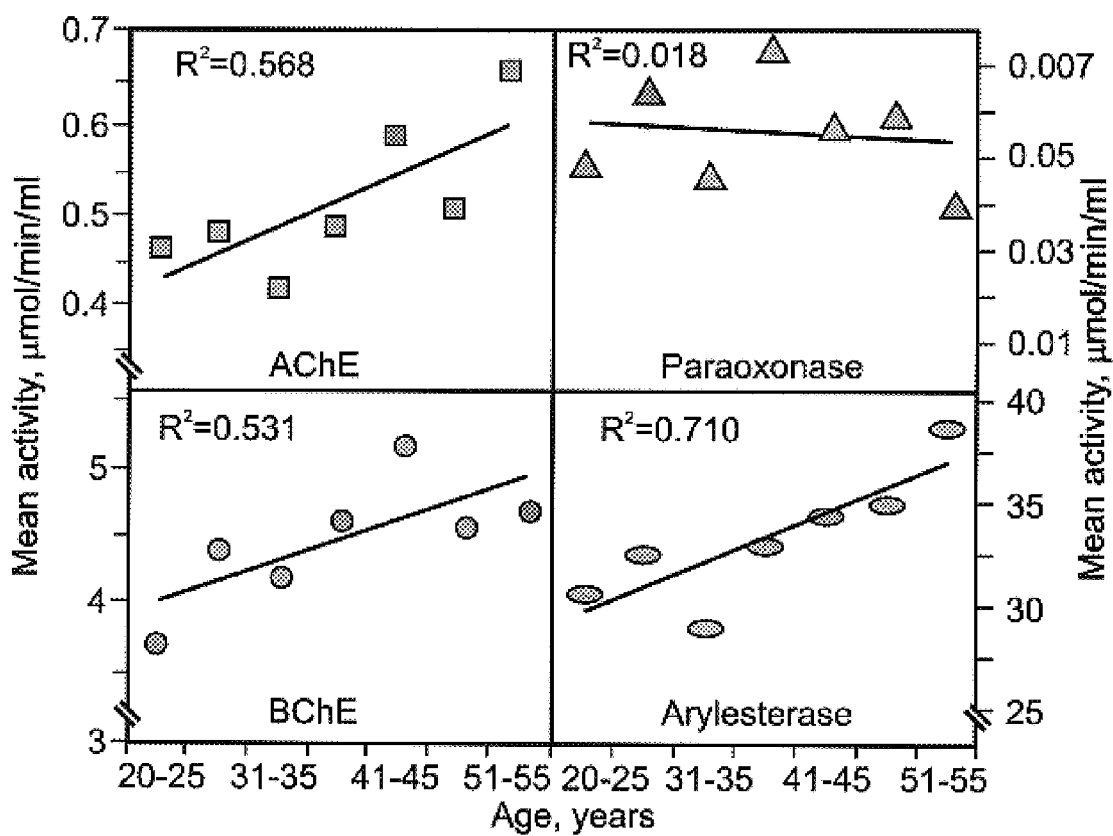

Further, enzyme activities were plotted as a function of age. Compatible with recent findings in US populations, (Sklan et al., Proc Natl Acad Sci USA, 101(15):5512-7, 2004), there is an observed increase in AChE activity with age (by ca. 20% between 20 and 55 years of age, $R^2=0.568$). A similar correlation was noted for BChE ($R^2=0.531$) and arylesterase ($R^2=0.710$) but not for PON1 ($R^2=0.018$) activities (FIG. 7B). This, in turn, suggested distinct genotype and/or environmental effects for the paraoxonase and arylesterase activities of the PON1 protein.

Example 7

Structure-function Relationships of PON1 Polymorphisms

A recently published X-Ray crystal structure of PON1 offers an explanation for the change in enzyme activity of the L55M polymorphism.

Figure 8A:
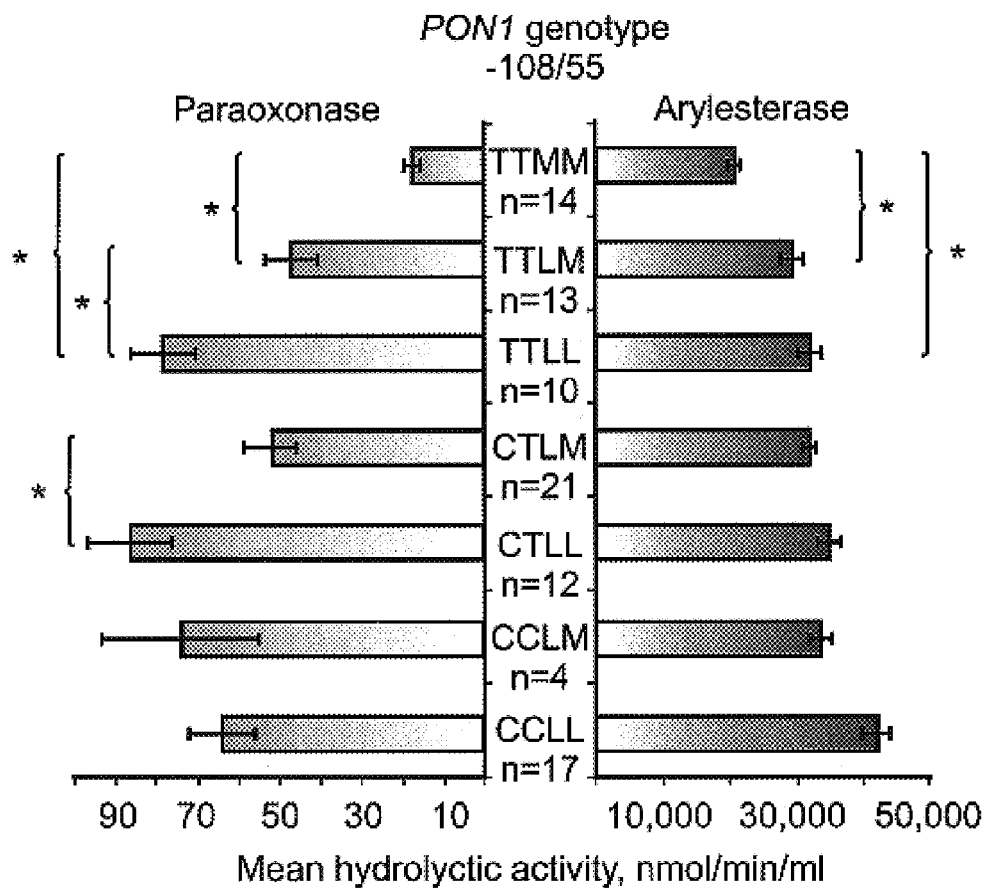

Homozygous carriers of PON1 Q192 with ML or LL genotypes displayed 29.2±11.0 and 47.8±9.5 nmol/min/ml paraoxonase and 20.1±5.1 and 28.7±7.4 μmol/min/ml arylesterase, respectively (p=0.0001, p=0.005). Thus, the 55L allele is associated with high and 55M with low paraoxonase and arylestease activity. Also, subjects homozygous for –108 CC with the 55 ML or 55 LL genotype displayed 21.0±3.6 or 26.1±9.3 arylesterase values (p=0.098). In subjects homozygous for –108 TT, however, activities were 20.0±5.0, 18.4±5.1 and 13.0±3.0 for LL, ML and MM carriers, reflecting p<0.002 and p<0.004 between the LL and MM genotypes and LM and MM carriers (FIG. 8A). Thus, unlike the findings of others, (Brophy et al., Am J Hum Genet, 68(6):1428-36, 2001) the L55M polymorphism showed an independent effect on enzyme activity, which in this study occurred regardless of the PON1 promoter composition. The rare MM genotype at position 55 appeared in this cohort only with TT at position –108.

The recently published X-ray structure of bacterial produced PON1 variants provided the opportunity of predicting the structural effects of the L55M substitution by modeling these two amino acid residues into the PON1 structure (PDB code 1V04). The structure of PON1 [PDB code 1V04] was the template for the following calculations. The substitution at positions L55 and K192 (L55M and Q192R) were applied using Deep View (spdbv v3.7). Steric clashes were initially resolved manually prior to energy minimization. Model superposition was done using Deep View spdbv 3.7. The structure of the complex Acetylcholinesterase-VX [PDB code 1 VXR] was the template for the docking paraoxon moiety in the active site of AChE.

Figure 8B:
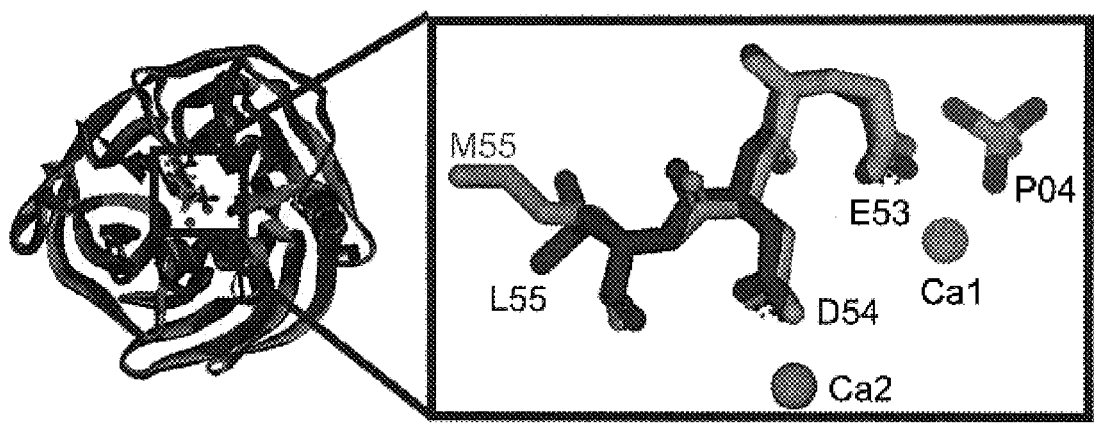

The PON1 protein is a β-propeller composed of six blades, each made of four densely packed β strands. The entire structure is held together by a disulfide bridge between cysteines 42 and 353. The methionine 55 side chain is positioned in the same direction as the leucine, without any steric clashes with other neighboring amino acid side chains. Nevertheless, energy minimization and superimposition (using SwisPDB Viewer) suggested changes in psi and phi dihedral angels of the residues adjacent to the leucine mutant (D54 and E53), which coordinate the two $Ca^{2+}$ ions involved with PON1 activity (FIG. 8B). The experimental data, which demonstrates considerably weaker hydrolytic activity for the M55 variant, supports this hypothesis.

Example 8

Genotype and Age-associated Increase in Arylesterase

Figure 9:
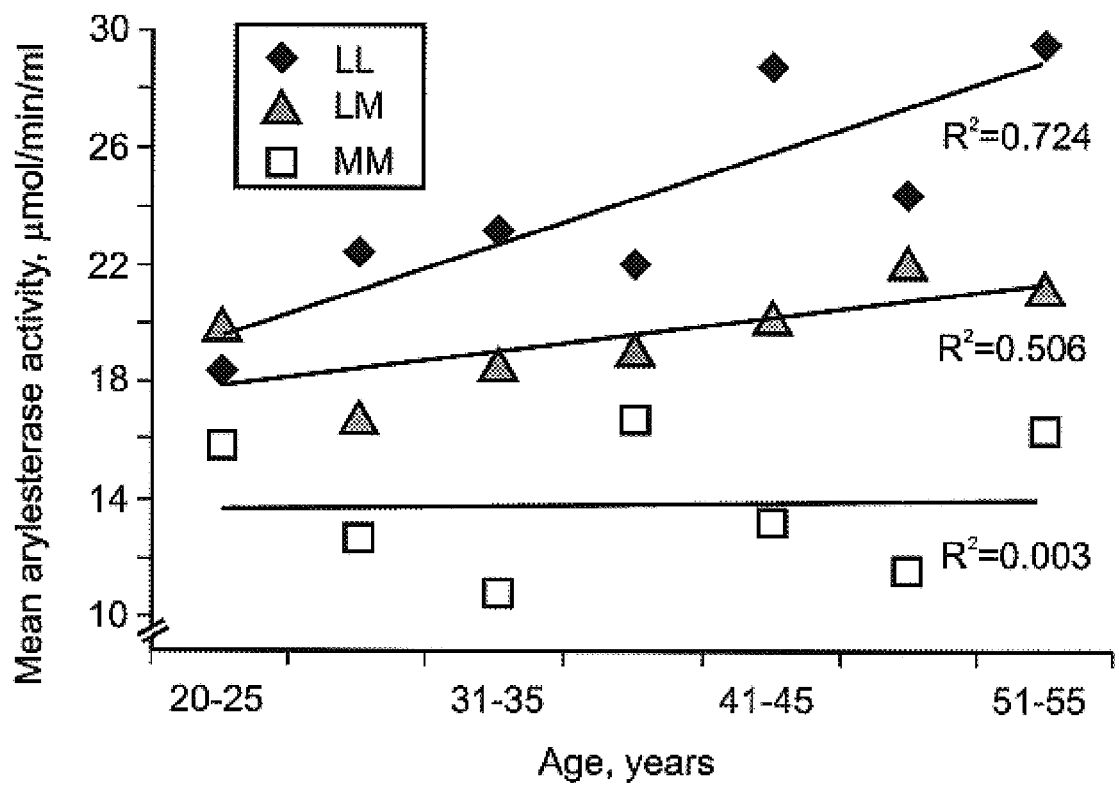

To explore the possibility of gene-environment interactions in the context of PON1 polymorphisms, PON1 activities were plotted as a function of age, following sub-classification into carriers of the 55 LL, LM and MM genotypes (FIG. 9). LL homozygotes showed an age-dependent increase ($R^2=0.724$, $y=1.54x+17.9$), LM heterozygotes displayed less age-dependent increase ($R^2=0.506$, $y=0.57x+17.4$) and MM homozygotes showed no increase ($R^2=0.003$, $y=0.06x+13.6$), suggesting gene dose dependence reflecting causal involvement for the 55L variant with this age-associated increase. 192 RR and QR subjects also showed a similar trend, however, when 55LL individuals were excluded from the QR population this trend was lost completely (data not shown), suggesting linkage to LL.

Example 9

Genotype and Substrate Specificity in Paraoxonase

The ability of paraoxonase to degrade organophosphates depends on the identity of the substrate and the genotype at the 192 position. These characteristics largely reflect the 192 substitution: the 192R variant hydrolyzes paraoxon more efficiently than the 192Q variant, (Davies et al., Nat Genet, 14(3):334-6, 1996) whereas diazoxon, sarin, and soman are better substrates for 192Q than for 192R. Phenyl acetate and chlorpyrifos oxon are hydrolyzed equally well by either of these two 192 alleles (FIG. 10A, Costa et al., Annu Rev Med, 54:371-92, 2003). PON1 structural analyses revealed a structural basis for the substrate specificity differences between the Q192 and 192R variants (FIG. 10B).

The large and positively charged arginine side chain at position 192 of paraoxonase interacts with paraoxon's negatively charged $NO_2$ group and thus contributes to paraoxon's rate of substrate hydrolysis. The interaction between the R192 side chain and the paraoxon nitro group increase the electron withdrawing properties of the latter and results in increased leaving group propensity of the corresponding p-nitro phenyl moiety. Glutamine at the same position can not facilitate such events for the paraoxon leaving group in the same manner, as demonstrated in FIG. 10B. Subclassification of the tested subjects by their Q192R genotypes supports this prediction, demonstrating gene dose-dependent increases of paraoxonase activity for 192R carriers (FIG. 10C).

Example 10

Genotype-phenotype Interactions of AChE and PON1

Complex genotype-phenotype correlations were also found for AChE. In transfected cells and immortalized lim- phoblasts from two carriers, the promoter deletion ΔHNF3☐ was associated with constitutive AChE overexpression (Shapira et al., Hum Mol Genet 9(9):1273-81, 2000). In this current sample, one of the four ΔHNF3β carriers displayed plasma AChE activity of 488 nmol/min/ml, similar to the average population (490±182 nmol/min/ml, n=91). Two other carriers had considerably lower than average AChE activities (239 and 167 nmol/min/ml), indicating that additional factors influence AChE activity in ΔHNF3β carriers. As suggested by the sensitivity of AChEs to oxidative stress, tested individuals with low PON1 activities displayed significantly higher AChE activities than those with high PON1 activity ($p<0.05$, FIG. 11B). No relationship was detected between BChE or arylesterase and PON1. Under sub-acute pesticide exposure, AChE competes with PON1 on paraoxon interactions, with $k_i$ of $97*10-4$ $M^{-1}min^{-1}$ for AChE, (Ordentlich et al., J Biol Chem, 273(31):19509-19517, 1998) as compared to $K_m$ of 0.27-0.5 mM for PON1 (Draganov, D. I. & B. N. La Du, Naunyn Schmiedebergs Arch Pharmacol, 369 (1):78-88, 2004). Paraoxon interactions with AChE lead to irreversible diethylphosphorylation of S200 in AChE's active site (FIG. 11A) (Sussman et al., Science, 253(5022):872-9, 1991). This, in turn, elevates acetylcholine levels. In brain and muscle, such reactions lead to increased AChE activities due to a feedback response of AChE overproduction (Kaufer et al., Nature, 393(6683):373-7, 1998).

The ACHE gene yields 3 different C-terminal variants: the primary one yields tetramers, the erythrocyte-associated one is not expected in plasma and the exposure- and stress-induced one occurs in monomers (Sklan et al., Proc Natl Acad Sci USA, 101(15):5512-7, 2004). In order to determine which AChE variants appear in plasma, native gel electrophoresis was employed followed by activity staining to detect catalytically active AChE.

Plasma (2 ☐l per lane) was electrophoresed in 7% non-denaturing polyacrylamide gel (Bio-Rad); catalytically active cholinesterase was stained according to the Karnovsky and Roots method [Sklan, 2004 #1795]. $5·10^{-5}$ M tetraisopropyl pyrophosphoramide (iso-OMPA, Sigma), was used to inhibit BChE. Controls included purified BChE from human serum (Sigma), recombinant human AChE-S (Sigma) and protein extract from COS-1 cells transfected with an expression vector encoding for the human AChE-R protein.

Alternatively, the resolved AChE can be visualized by immunoblot analysis. For example, rabbit polyclonal antibodies against the carboxyl-terminal sequence of human AChE-R have been described. After incubating the blot with the primary antibody for an appropriate period of time and washing to reduce non-specific binding, biotinylated donkey anti-rabbit antibodies are used as secondary antibodies. The biotinylated secondary antibody can be visualized by suitable means such as Streptavidin-HRP.

The slowly migrating band in plasma (FIG. 11C, arrowhead) was inhibitable by iso-OMPA (data not shown), indicating the presence of BChE. Subjects with relatively high AChE activity presented higher levels of rapidly migrating, monomeric fractions, presumably intact and C-terminally truncated versions of AChE-R (FIG. 11C, Cohen et al., J Mol Neurosci, 21(3):199-212, 2003). BChE (Sigma), from human serum, however, did not show any fast migrating bands, unlike the recombinant monomeric AChE-R. This supported the working hypothesis by extending the AChE-R feedback response to the circulation and suggested that higher values of AChE plasma activities largely reflected gene expression modulations. The descriptions given are intended to exemplify, but not limit, the scope of the invention. Other embodiments are within the claims.

Example 11

Serum Cholinergic Activity in Essential Hypertension

Essential hypertension occurs when the systolic pressure is consistently over 140 mm Hg, or the diastolic blood pressure is consistently over 90 mm Hg with no identifiable cause. Patients are at risk of heart attacks, congestive heart failure, atherosclerosis, kidney damage, stroke and loss of vision. It has been suggested that anxiety is associated with essential hypertension (Blumenthal, et al J Psychosom. Res 1995; 39:133-144; McGarry et al, J Behav Med 1990; 13:93-101). In order to further explore the association between anxiety and cholinergic enzyme activities, serum levels of 4 cholinergic enzyme activities (AChE, BChE, PON1 and arylesterase) were compared in hypertensive and normal subjects.

Cholinergic enzyme activity was assayed as described hereinabove in serum samples from the jugular vein (JV), carotid sinus (CS), and Aorta, at two time points (A0 and A1), in 6 hypertensive and 4 matched normal patients. AChE showed approximately a 60% increase (P<0.001) in all sampling sites (FIG. 13A), arylesterase (FIG. 13C) and PON1 (FIG. 13D) activity showed significant increases in all sampling sites as well, whereas BChE showed no change (FIG. 14D). No significant differences were observed in AChE or BChE activity (FIGS. 14A and 14B). Treatment resulted in a slight but consistent reduction in PON1 activity at all sites assayed (FIG. 14D).

Using the regression analysis described in Example 4, D and E, hereinabove, for the prediction of anxiety in the general population, Trait and Sate anxiety scores of the depressed patients were predicted on the basis of cholinergic activity and demographic data, before and after treatment, and then compared with actual STAI questionnaire scores. Table 8 below shows the observed anxiety scores vs. the predicted scores.

TABLE 8

| | State anxiety | | | | Trait anxiety | | | |
|---|---|---|---|---|---|---|---|---|
| | Predicted Treated | Observed Treated | Predicted Untreated | Observed Untreated | Predicted Treated | Observed Treated | Predicted Untreated | Observed Untreated |
| 1 | 24 | 41 | 25 | 36 | 55 | 62 | 56 | 69 |
| 2 | 21 | 30 | 22 | 60 | 48 | 40 | 49 | 66 |
| 3 | 23 | 27 | | 48 | 53 | 48 | | 66 |
| 4 | 23 | 39 | 24 | 38 | 52 | 34 | 53 | 50 |
| 5 | 21 | 31 | 25 | 51 | 51 | 33 | 53 | 54 |
| 6 | 25 | 28 | | 64 | 55 | 30 | | 63 |
| 7 | 21 | 50 | 16 | 62 | 49 | 50 | 45 | 55 |
| 8 | 20 | 50 | 22 | 56 | 51 | 53 | 52 | 66 |
| 9 | 21 | 61 | | 77 | 50 | 56 | | 71 |
| 10 | 22 | 46 | 23 | 65 | 51 | 60 | 52 | 71 |
| 11 | 21 | | 20 | 52 | 51 | | 51 | 65 |
| 12 | 23 | 44 | 25 | 55 | 52 | 51 | 53 | 60 |
| 13 | 22 | 28 | 22 | 57 | 51 | 39 | 51 | 55 |
| 14 | 21 | 41 | 22 | 54 | 50 | 43 | 50 | 59 |
| Av | 22 | 40 | 22 | 55 | 51 | 46 | 51 | 62 |
| stdev | 1.57 | 10.54 | 2.77 | 10.62 | 2.11 | 10.44 | 2.81 | 6.72 |
| sem | 0.42 | 2.92 | 0.84 | 2.84 | 0.56 | 2.90 | 0.85 | 1.80 |
| P value (chitest) | 2.60043E−18 | | 1.03288E−36 | | 2.685E−06 | | 0.0418554 | |

13B). No differences were observed between the enzyme activities at different sites (JV, CS, A), or time points (A0 vs. A1).

Thus, these results show that serum cholinergic enzyme activities (specifically, PON1, arylesterase and AChE) are increased in hypertension, thus their assay may be used to indicate and monitor hypertension related anxiety.

Example 12

Serum Cholinergic Activity in Depression

Depression and anxiety are commonly linked in emotional disorders, and patients often exhibit symptoms which are common to both depression and anxiety (Dunner, Depress Anxiety 2001; 13:57-71). In order to further explore the association between depression and anxiety, and to test the predictive value of cholinergic enzyme activities for trait and state anxiety, serum levels of 4 cholinergic enzyme activities (AChE, BChE, PON1 and arylesterase) were compared in depressed patients, before and after receiving treatment for psychologically assessed depression.

Cholinergic enzyme activity was assayed as described hereinabove in serum samples from the jugular vein (JV), carotid sinus (CS), and Aorta, at two time points (A0 and A1), in 14 patients. FIGS. 14A-14D show the average values of the cholinergic enzyme activity in the serum, compared to matched controls. Average enzyme activity of PON1 and arylesterase in the depressed patients was greater than controls, both before and following treatment (FIGS. 14C and FIG. 15 shows the average Trait and State anxiety scores of the depressed patients, before and after treatment, compared with the average predicted anxiety scores. In general, treatment for the depression produced reduced scores for both State and Trait anxiety. The average observed scores for State and Trait anxiety before treatment are higher than those predicted from serum cholinergic activity, more so for State than Trait anxiety scores. Treatment ameliorated part of the differences between predicted and observed State anxiety scores, while treatment inverted the differences between predicted and observed Trait anxiety scores.

Without wishing to be limited to a single hypothesis, it is conceivable that the generally higher observed than predicted anxiety scores in depressed patients indicates that prediction from cholinergic activity and demographic data, using the equations of Example 4, D and E, delimits the anxiety measures found in healthy individuals.

Thus, these results show that assaying cholinergic enzyme activities in depression, especially PON1 and arylesterase, can be used to assess depression-related anxiety, and for assessment and prediction of treatment efficacy and outcome, as it relates to anxiety, in such disease-related anxiety. Further, these results support the predictive value of measurement of cholinergic enzymes for detection of differences from normal scale anxiety values.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of assessing trait anxiety in a subject, the method comprising
   providing a test sample from said subject;
   determining acetylcholinesterase (AChE) activity in said test sample; and
   comparing AChE activity in said test sample to AChE activity in a reference sample derived from one or more individuals whose trait anxiety level is known, wherein said one or more individuals in said reference sample are similar to said subject in at least one trait selected from the group consisting of gender, age, race, ethnic group, and body mass index, and wherein a lower level of AChE activity in said test sample compared to AChE activity in said reference sample indicates said subject has greater trait anxiety than the trait anxiety level of said one or more individuals from which the reference sample was derived,
   thereby assessing trait anxiety in said subject.

2. The method of claim 1, further comprising determining paraoxonase (PON) activity in said test sample; and
   comparing PON activity in said test sample to PON activity in a reference sample derived from one or more individuals whose trait anxiety level is known.

3. The method of claim 1, further comprising determining pseudocholinesterase (BChE) activity in said test sample; and
   comparing BChE activity in said test sample to BChE activity in a reference sample derived from one or more individuals whose trait anxiety level is known.

4. The method of claim 1, wherein said anxiety is situational anxiety.

5. The method of claim 4, wherein said anxiety is depression-related anxiety.

6. The method of claim 4, wherein said anxiety is hypertension-related anxiety.

7. The method of claim 1, wherein said anxiety is non-situational anxiety.

8. A method of assessing trait anxiety in a subject, the method comprising providing a plurality of test samples from said subject, wherein said test samples are taken at different times from said subject;

determining AChE activity in said plurality of test samples; and comparing AChE activity of two or more test samples from said plurality of test samples, and wherein a lower level of AChE activity in any of said test samples compared to AChE activity in a test sample taken at a different time indicates greater trait anxiety in said subject at the time of sampling of the sample having a lower AChE level;

thereby assessing the trait anxiety in a subject over a period of time.

9. The method of claim 8, wherein comparing AChE activity comprises comparing AChE activity of one or more test samples taken at one or more timepoints during an anxiety attack and one or more test samples taken at one or more timepoints after an anxiety attack.

10. A method of determining susceptibility to state anxiety in a subject, the method comprising:

providing a test sample from said subject;

determining PON activity in said subject;

comparing PON activity in said test sample to the amount of PON activity in a reference sample derived from one or more individuals whose state anxiety, level is known, wherein said one or more individuals in said reference sample are similar to said subject in at least one trait selected from the group consisting of gender, age, race, ethnic group, and body mass index, and wherein lower PON activity in said test sample relative to said reference sample indicates said subject is at increased susceptibility for developing state anxiety than said one or more individuals in said reference sample;

thereby determining susceptibility to state anxiety in said subject.

11. A method of assessing state anxiety in a subject, the method comprising providing a plurality of test samples from said subject, wherein said test samples are taken at different times from said subject;

determining PON activity in said plurality of test samples; and comparing PON activity of two or more test samples from said plurality of test samples, wherein a lower level of PON activity in any of said test samples compared to PON activity in a test sample taken at a different time indicates greater susceptibility to state anxiety in said subject at the time of sampling of the sample having a lower PON level;

thereby assessing state anxiety in a subject over a period of time.

12. The method of claim 11, wherein comparing PON activity comprises comparing PON activity of one or more test samples taken at one or more timepoints before administering an anxiety treatment and one or more test samples taken at one or more timepoints after administering an anxiety treatment.

13. The method of claim 11, wherein comparing PON activity comprises comparing PON activity of one or more test samples taken at one or more timepoints during an anxiety attack and one or more test samples taken at one or more timepoints after an anxiety attack.

14. A method of assessing trait or state anxiety in a subject, the method comprising determining in a biological sample of the subject a level of expression and/or activity of at least one serum cholinesterase (ChE) and paraoxonase (PON1); and correlating between said levels of expression and/or activity of said at least one serum cholinesterase and said paraoxonase, wherein a serum ChE/PON expression or activity level ratio above or below a predetermined threshold is indicative of trait or state anxiety, thereby assessing trait or state anxiety in the subject.

15. The method of claim 14, wherein said determining said expression level of said at least one serum cholinesterase (ChE) and said paraoxonase (PON1) is determining an mRNA level of said serum ChE and said PON.

16. The method of claim 14, wherein said at least one cholinesterase (ChE) is Acetylcholinesterase (AChE).

* * * * *